US009587220B2

(12) United States Patent
Nakatsuji et al.

(10) Patent No.: US 9,587,220 B2
(45) Date of Patent: Mar. 7, 2017

(54) METHOD FOR INDUCING CARDIAC DIFFERENTIATION OF PLURIPOTENT STEM CELL

(71) Applicant: Kyoto University, Kyoto-shi (JP)

(72) Inventors: Norio Nakatsuji, Kyoto (JP); Itsunari Minami, Kyoto (JP); Motonari Uesugi, Kyoto (JP); Kazuhiro Aiba, Kyoto (JP)

(73) Assignee: KYOTO UNIVERSITY, Kyoto-Shi (JP)

( * ) Notice: Subject to any disclaimer, the term of this patent is extended or adjusted under 35 U.S.C. 154(b) by 0 days.

(21) Appl. No.: 14/374,453

(22) PCT Filed: Jan. 25, 2013

(86) PCT No.: PCT/JP2013/051644
§ 371 (c)(1),
(2) Date: Jul. 24, 2014

(87) PCT Pub. No.: WO2013/111875
PCT Pub. Date: Aug. 1, 2013

(65) Prior Publication Data
US 2015/0017718 A1    Jan. 15, 2015

Related U.S. Application Data

(60) Provisional application No. 61/591,805, filed on Jan. 27, 2012.

(51) Int. Cl.
C12N 5/02 (2006.01)
C12N 5/074 (2010.01)
C12N 5/077 (2010.01)
C07D 277/82 (2006.01)
C07D 495/04 (2006.01)

(52) U.S. Cl.
CPC ......... *C12N 5/0657* (2013.01); *C07D 277/82* (2013.01); *C07D 495/04* (2013.01); *C12N 2501/415* (2013.01); *C12N 2506/02* (2013.01); *C12N 2506/45* (2013.01)

(58) Field of Classification Search
None
See application file for complete search history.

(56) References Cited

U.S. PATENT DOCUMENTS

| 4,970,318 | A | 11/1990 | Schnur et al. |
| 2003/0134859 | A1 | 7/2003 | Amemiya et al. |
| 2006/0276393 | A1 | 12/2006 | Milburn et al. |
| 2007/0134215 | A1 | 6/2007 | Fukuda et al. |
| 2007/0148185 | A1 | 6/2007 | Rathore et al. |
| 2007/0149466 | A1 | 6/2007 | Milburn et al. |
| 2009/0068742 | A1 | 3/2009 | Yamanaka |
| 2009/0170914 | A1 | 7/2009 | Bornancin et al. |
| 2010/0183565 | A1 | 7/2010 | Laflamme et al. |
| 2012/0244619 | A1 | 9/2012 | Nakatsuji et al. |
| 2013/0183753 | A1 | 7/2013 | Nakatsuji et al. |
| 2013/0274215 | A1* | 10/2013 | Thies ............. A61K 31/00 514/30 |
| 2014/0127807 | A1 | 5/2014 | Nakatsuji et al. |
| 2015/0017718 | A1 | 1/2015 | Nakatsuji et al. |
| 2016/0002600 | A1 | 1/2016 | Nakatsuji et al. |

FOREIGN PATENT DOCUMENTS

| EP | 2014766 A1 | 1/2009 |
| JP | S63-190880 A | 8/1988 |
| JP | H02-017181 A | 1/1990 |
| JP | 2000-508919 A | 7/2000 |
| JP | 2001-510450 A | 7/2001 |
| JP | 2004-535199 A | 11/2004 |
| JP | 2005-330443 A | 12/2005 |
| JP | 2006-218035 A | 8/2006 |
| JP | 2007-252220 A | 10/2007 |
| JP | 2009-500357 A | 1/2009 |
| JP | 2009-531365 A | 9/2009 |
| WO | 97/41209 A1 | 11/1997 |
| WO | 98/17267 A1 | 4/1998 |
| WO | 01/83427 A1 | 11/2001 |
| WO | 03/006950 A2 | 1/2003 |
| WO | 2005/037845 A1 | 4/2005 |
| WO | 2007/069666 A1 | 6/2007 |
| WO | 2007/070964 A1 | 6/2007 |
| WO | 2008/118820 A2 | 10/2008 |
| WO | 2009/006930 A1 | 1/2009 |
| WO | 2009/006997 A1 | 1/2009 |
| WO | 2009/007852 A2 | 1/2009 |
| WO | 2011/002950 A1 | 1/2011 |
| WO | 2011/071118 A1 | 6/2011 |

(Continued)

OTHER PUBLICATIONS

Paige et al, Endogenous Wnt/b-Catenin Signaling is Required for Cardiac Differentiation in Human Embryonic Stem Cells, PLoS One, 2010, pp. 1-8.*
Biechele et al, Porcupine homolog is required for canonical Wnt signaling and gastrulation in mouse embryos, Developmental Biology 355 (2011) 275-285.*
Okita et al Induced pluripotent stem cells:opportunities and challenges, Phil. Trans. R. Soc. B (2011) 366, 2198-2207.*
U.S. Appl. No. 14/154,765, filed Jan. 14, 2014, Method for Promoting Differentiation of Pluripotent Stem Cells into Cardiac Muscle Cells.
Asai, Y., Tada, M., Otsuji, T.G. & Nakatsuji, N. Combination of functional cardiomyocytes derived from human stem cells and a highly-efficient microelectrode array system: an ideal hybrid model assay for drug development. Curr Stem Cell Res Ther 5, 227-232 (2010).
Bellasio et al., Substances with potential cardiovascular activity. 2-Acylaminobenzimidazoles with hypotensive activity, Farmaco, Edizione Scientifica, 1973, vol. 28, No. 20, abstract only.

(Continued)

*Primary Examiner* — Maria Marvich
(74) *Attorney, Agent, or Firm* — Fox Rothschild LLP

(57) ABSTRACT

The present invention relates to a method for inducing cardiac differentiation of a pluripotent stem cell, which comprises the steps of
(1) culturing a pluripotent stem cell in a medium containing one or more WNT signaling activators, and
(2) culturing a cell produced in the step (1) in a medium containing one or more WNT signaling inhibitor.

18 Claims, 14 Drawing Sheets

(56) References Cited

FOREIGN PATENT DOCUMENTS

| WO | 2012/026491 A1 | 3/2012 |
|---|---|---|
| WO | 2013/111875 A1 | 8/2013 |
| WO | 2014/136519 A1 | 9/2014 |

OTHER PUBLICATIONS

Berge ten Derk, et al., "Embryonic stem cells require Wnt proteins to prevent differentiation to epiblast stem cells", Nature Cell Biol., 2011, vol. 13, No. 9, p. 1070-1075.

Burridge, P.W. et al. A universal system for highly efficient cardiac differentiation of human induced pluripotent stem cells that eliminates interline variability. PLoS One 6, e18293 (2011).

Carlton et al., "Discovery of small molecule agonists for the bombesin raceotor subtype 3 (BRS-3) based on an omeprazole lead", Bioorganic & Medicinal Chemistry Letters, 2008, vol. 8. No. 20, pp. 5451-5455.

Chen, B. et al. Small molecule-mediated disruption of Wnt-dependent signaling in tissue regeneration and cancer. Nat Chem Biol 5, 100-107 (2009).

Chien, K.R., Domian, I.J. & Parker, K.K. Cardiogenesis and the complex biology of regenerative cardiovascular medicine. Science 322, 1494-1497 (2008).

Chien, K.R., Moretti, A. & Laugwitz, K.L. Development. ES cells to the rescue. Science 306, 239-240 (2004).

Database Registry [online]:Chemical Abstracts Service, Columbus, Ohio, USA. [retrieved on Feb. 19, 2013] Retrieved from STN, Registry Number(Entry Date): 1177562-46-7(Aug. 30, 2009), 1136531-24-2(Apr. 19, 2009) , 1136432-3.4-2(.Apr. 19, 2009) , 1023259-74-6(May 28, 2008).

Hansson, E.M., Lindsay, M.E. & Chien, K.R. Regeneration next: toward heart stem cell therapeutics. Cell Stem Cell 5, 364-377 (2009).

Hao, J. et al. Dorsomorphin, a selective small molecule inhibitor of BMP signaling, promotes cardiomyogenesis in embryonic stem cell. PLoS One 3, e2904 (2008).

Harsanyi et al., "Reactions of acylcyanomides. I. New synthesis of 2-acylaminobenzoxazoles", Annali di Chimica (Rome, Itary), 1964, vol. 54, No. 11, pp. 1060-1065.

Ichida, J.K. et al. A small-molecule inhibitor of tgf-Beta signaling replaces sox2 in reprogramming by inducing nanog. Cell Stem Cell 5, 491-503 (2009).

Irion, S., Nostro, M.C., Kaftman, S.J. & Keller, G.M. Directed differentiation of pluripotent stem cells: from developmental biology to therapeutic applications. Cold Spring Harb Symp Quant Biol 73, 101-110 (2008).

Jacot, J.G., Martin, J.C. & Hunt, D.L. Mechanobiology of cardiomyocyte development. J Biomech 43, 93-98 (2010).

Kamisuki, S. et al. A small molecule that blocks fat synthesis by inhibiting the activation of SREBP. Chem Biol 16, 882-892 (2009).

Kattman, S.J. et al. Stage-specific optimization of activin/nodal and BMP signaling promotes cardiac differentiation of mouse and human pluripotent stem cell lines. Cell Stem Cell 8, 228-240 (2011).

Laflamme, M.A. & Murry, C.E. Heart regeneration. Nature 473, 326-335 (2011).

Leschik et al.,"Cardiac commitment of primate embryonic stem cells", Nature Protocos, 2008, vol. 3, No. 9, pp. 1381-1387.

Lluis Frederic, et al., "Periodic Activation of Wnt/?-Catenin Signaling Enhances Somatic Cell Reprogramming Mediated by Cell Fusion", Cell Stem Cell, 2008, Vol.3, p. 493-507.

Lutolf, M.P., Gilbert, P.M. & Blau, H.M. Designing materials to direct stem-cell fate. Nature 462, 433-441 (2009).

Menasche, P. Stem cell therapy for heart failure: are arrhythmias a real safety concern? Circulation 119, 2735-2740 (2009).

Mignone, J.L., Kreutziger, K.L., Paige, S.L. & Murry, C.E. Cardiogenesis from human embryonic stem cells. Circ J 74, 2517-2526 (2010).

Mummery et al., "Differentiation of Human Embryomic Stem Cells to Cardiomyocytes: Role of Coculture With Visceral Endoderm-Like Cells", Circulation, American Heart Association, 2003, 107, pp. 2733-2740.

Murakami, G. et al. Chemical library screening identifies a small molecule that downregulates SOD1 transcription for drugs to treat amyotrophic lateral sclerosis. J Biomol Screen 16,405-414 (2011).

Naito, A.T. et al. Developmental stage-specific biphasic roles of Wnt/beta-catenin signaling in cardiomyogenesis and hematopoiesis. Proc Natl Acad Sci U S A 103, 19812-19817 (2006).

Otsuji, T.G. et al. Progressive maturation in contracting cardiomyocytes derived from human embryonic stem cells: Qualitative effects on electrophysiological responses to drugs. Stem Cell Res 4, 201-213 (2010).

Paige, S.L. et al. Endogenous Wnt/beta-catenin signaling is required for cardiac differentiation in human embryonic stem cells. PLoS One 5, e11134 (2010).

Passier, R., van Laake, L.W. & Mummery, C.L. Stem-cell-based therapy and lessons from the heart. Nature 453, 322-329 (2008).

Qyang, Y. et al. The renewal and differentiation of Isl1+ cardiovascular progenitors are controlled by a Wnt/beta-catenin pathway. Cell Stem Cell 1, 165-179 (2007).

Rajala, K., Pekkanen-Mattila, M. & Aalto-Setala, K. Cardiac differentiation of pluripotent stem cells. Stem Cells Int 2011, 383709 (2011).

Ren, Y. et al. Small molecule Wnt inhibitors enhance the efficiency of BMP-4-directed cardiac differentiation of human pluripotent stem cells. J Mol Cell Cardiol 51, 280-287 (2011).

Sato, A., Kawazoe, Y., Kamisuki, S. & Uesugi, M. Synthesis of synthetic small molecule transcription factors (STF). Nucleic Acids Symp Ser (Oxf), 29-30 (2006).

Sato, S., Murata, A., Shirakawa, T. & Uesugi, M. Biochemical target isolation for novices: affinity-based strategies. Chem Biol 17, 616-623 (2010).

Sci Planner 2013, Chemical Abstracts Service, Columbus, OH,: RN-1118807-13-8 Downloaded Sep. 24, 2013.

Sci Planner 2013, Chemical Abstracts Service, Columbus, OH,: RN-349132-98-5 Downloaded Sep. 27, 2013.

Segers, V.F. & Lee, R.T. Stem-cell therapy for cardiac disease. Nature 451, 937-942 (2008).

Shamblott, et al., "Derivation of pluripotent stem cells from cultured human primordial germ cells" Proc. Natl. Acad. Sci. USA vol. 95, pp. 13726-13731, Nov. 1998.

Smith, K. P. et al., Pluripotency: toward a gold standard for human ES and iPS cells, J Cell Physiol 220, 21-29 (2009).

Srivastava, D. & Ivey, K.N. Potential of stem-cell-based therapies for heart disease. Nature 441, 1097-1099 (2006).

STN Columbus search result of STN-Registry data base for RN:308294-59-9, RN:349132-90-7, 'RN:805285-70-5', RN:349438-98-8H, 'RN:953930-375', RN;953995-50-1 and RN:953993-61-8, access date Mar. 28, 2014.

Stuckwisch et al., "Some N-Substituted Dimethoxyphenyl-acetamides and Dimethoxyphenylethylamines", Jounal of Medicinal Chmistry, 1965, vol. 8, issue 5, pp. 734-735.

Suemori, H. & Nakatsuji, N. Generation and characterization of monkey embryonic stem cells. Methods Mol Biol 329, 81-89 (2006).

Suemori, H. et al. Efficient establishment of human embryonic stem cell lines and long-term maintenance with stable karyotype by enzymatic bulk passage. Biochem Biophys Res Commun 345, 926-932 (2006).

Suemori, H. et al. Establishment of embryonic stem cell lines from cynomolgus monkey blastocysts produced by IVF or ICSI. Dev Dyn 222, 273-279 (2001).

Suessbrich, H., Waldegger, S., Lang, F. & Busch, A.E. Blockade of HERG channels expressed in Xenopus oocytes by the histamine receptor antagonists terfenadine and astemizole. FEBS Lett 385, 77-80 (1996).

Takahashi, K. et al. Induction of pluripotent stem cells from adult human fibroblasts by defined factors. Cell 131, 861-872 (2007).

Thomson, J.A. et al. Embryonic stem cell lines derived from human blastocysts. Science 282, 1145-1147 (1998).

(56) References Cited

OTHER PUBLICATIONS

Toyama, "ES Saibo x iPS Saibo kara no Shinkin Saibo Bunka x Seisei x ishoku", Japaese Jounal of Transplantation, 2009, vol. 44, No. 3, pp. 219-225.
Wang, H., Hao, J. & Hong, C.C. Cardiac induction of embryonic stem cells by a small molecule inhibitor of Wnt/beta-catenin signaling. ACS Chem Biol 6, 192-197 (2011).
Willems, E. et al. Small-molecule inhibitors of the Wnt pathway potently promote cardiomyocytes from human embryonic stem cell-derived mesoderm. Circ Res 109, 360-364 (2011).
Xu et al., "Chemicallu defined medium supporting cardiomyocyte differentiation of human embryonic stem cells", Differentiation (2008) 76:958-970.
Xu, Y., Shi Y. & Ding, S. A chemical approach to stem-cell biology and regenerative medicine. Nature 453, 338-344 (2008).
Yamashita, J.K. ES and iPS cell research for cardiovascular regeneration. Exp Cell Res 316, 2555-2559 (2010).
Yang, L. et al. Human cardiovascular progenitor cells develop from a KDR+ embryonic-stem-cell-derived population. Nature 453, 524-528 (2008).
Yoshida, Y. & Yamanaka, S. iPS cells: a source of cardiac regeneration. J Mol Cell Cardiol 50, 327-332 (2011).
Yu, J. et al. Induced pluripotent stem cell lines derived from human somatic cells. Science 318, 1917-1920 (2007).
Yuasa, S. et al. "Transient inhibition of BMP signaling by Noggin induces cardiomyocyte differentiation of mouse embryonic stem cells" . Nat Biotechnol 23, 607-611(2005).
Zhu, W. et al. IGFBP-4 is an inhibitor of canonical Wnt signalling required for cardiogenesis. Nature 454, 345-349 (2008).
Doetshman T. et al., "Establishment of Hamster Blastocyst-Derived Embryonic Stem (ES) Cells", Dev. Biol. 127: 224-227 (1988).
Evans M. J. et al., "Derivation and Preliminary Characterization of Pluripotent Cell Lines from Porcine and Bovine Blastocysts", Theriogenology 33: 125-128 (1990).
Even, M.S., Sandusky, C.B. & Barnard, N.D. "Serum-free hybridoma culture: ethical, scientific and safety considerations", Trends Biotechnol 24, 105-108 (2006).
Feng et al., "Reprogramming of fibroblasts into induced pluripotent stem cells with orphan nuclear receptor Esrrb", Nature Cell Biology, 2009, vol. 11, pp. 197-203.
Gonzalez Rodolfo, et al., "Stepwise Chemically Induced Cardiomyocyte Specification of Human Embryonic Stem Cells", Angew. Chem. Int. Ed., 2011, Vol.50, p. 11181-11185.
Gotea, V. & Ovcharenko, I. "DiRE: identifying distant regulatory elements of co-expressed genes", Nucleic Acids Res 36, W133-139 (2008).
Graichen, R. et al. "Enhanced cardiomyogenesis of human embryonic stem cells by a small molecular inhibitor of p38 MAPK", Differentiation 76, 357-370 (2008).
Hanna et al., "Direct Reprogramming of Terminally Differentiated Mature B Lymphocytes to Pluripotency", Cell 133 (2): 250-264 (2008).
Huangfu et al., "Induction of pluripotent stem cells from primary human fibroblasts with only Oct4 and Sox2", Nature Biotechnology 26:1269-1275 (2008).
Kim et al., "Oct4-Induced Pluripotency in Adult Neural Stem Cells", Cell 136(3): 411-419 (2009).
Kim et al., "Pluripotent stem cells induced from adult neural stem cells by reprogramming with two factors", Nature 454: 646-650 (2008).
Notarianni E. et al., "Derivation of pluripotent, embryonic cell lines from the pig and sheep", J. Reprod. Fert. Suppl. 43: 255-260 (1991)).
Notarianni E. et al., "Maintenance and differentiation in culture of pluripotential embryonic cell lines from pig blastocysts", Journals of Reproduction & Fertility 41: 51-56 (1990).
Piedrahita J. A. et al., "On the isolation of embryonic stem cells: Comparative behavior of murine, porcine and ovine embryos", Theriogenology 34: 879-891 (1990).
Saito S. et al., "Bovine embryonic stem cell-like cell lines cultured over several passages", Roux. Arch. Dev. Biol. 201: 134-141 (1992).
Shi et al., "Induction of Pluripotent Stem Cells from Mouse Embryonic Fibroblasts by Oct4 and Klf4 with Small-Molecule Compounds", Cell Stem Cell 3(5): 568-574 (2008).
Sukoyan M. A. et al., "Isolation and Cultivation of Blastocyst-Derived Stem Cell Lines From American Mink (*Mustela vison*)", Morecula Rreproduction and Development,33: 41 8-431 (1992).
Talbot N. C. et al., "Culturing the epiblast cells of the pig blastocyst", Cell. Dev. Biol. 29A: 543-554 (1993).
Thomson J. A. et al., Pluripotent Cell Lines Derived from Common Marmoset (*Callithrix jacchus*) BlastocystsBiol. Reprod. 55: 254-259 (1996).
Thomson J. A. et al., "Isolation of a primate embryonic stem cell line", Proc. Natl. Acad. Sci. USA 92: 7844-7848 (1995).
Wada Keiki et al., "Hito Tanosei Kansaibo Kabu (ES Oyobi iPS Saibo Kabu) o Mochiita Bunka Yudo Gijutsu Oyobi HTS eno Oyo Tenkai", Medicine and Drug Journal, 2010, vol.46, S-1, pp. 247-253.
Zhao et al., "Two Supporting Factors Greatly Improve the Efficiency of Human iPSC Generation", Cell Stem Cell 3: 475-479 (2008).
Zhou et al., "Generation of Induced Pluripotent Stem Cells Using Recombinant Proteins", Cell Stem Cell 4(5): 381-384 (2009).
Minami et al, "A small molecule that promotes cardiac differentiation of human pluripotent stem cells under defined, cytokine- and xeno-free conditions." Cell Reports, vol. 2, No. 5, Nov. 29, 2012, pp. 1448-1460.
Extended European Search Report dated Aug. 7, 2015 issued in the corresponding European Patent Application No. 13740826.6.
Database Registry[Online]: Chemical Abstracts Service, Columbus, Ohio, USA. [retrieved on Oct. 7, 2011] Retrieved from STN, Registry Number(Entry Date): 1177562-46-7(Aug. 30, 2009), 1147532-35-1(May 19, 2009), 1147404-38-3(May 19, 2009) , 1147337-80-1 (May 19, 2009 ) , 1136531-24-2 (Apr 19, 2009), 1136432-34-2(Apr. 19, 2009), 1090781-93-3(Dec. 28, 2008), 1061194-02-2(Oct. 14, 2008), 1061020-56-1 (Oct. 14, 2008), 1031144-38-3 (Jun. 27, 2008), 1031127-32-8(Jun. 27, 2008), 1023259-74-6(May 28, 2008), 1017145-50-4(Apr. 25, 2008), 941864-24-0 (Jul. 10, 2007)
Lian, X., et al., "Robust cardiomyocyte differentiation from human pluripotent stem cells via temporal modulation of canonical Wnt signaling", Proc. Natl. Acad. Sci. USA 109, E1848-E1857, 2012.
PubChem CID 2694580—National Center for Biotechnology Information, PubChem Compound Database; CID=2694580, http://pubchem.ncbi.nlm.nih.gov/summary/summary.cgi?cid=2694580 (accessed Dec. 21, 2015), create date Jul. 16, 2005.
PubChem CID 2641096—National Center for Biotechnology Information, PubChem Compound Database; CID=2641096, http://pubchem.ncbi.nlm.nih.gov/summary/summary.cgi?cid=2641096 (accessed Dec. 21, 2015), create date Jul. 16, 2005.
PubChem CID 1358256—National Center for Biotechnology Information, PubChem Compound Database; CID=1358256, http://pubchem.ncbi.nlm.nih.gov/summary/summary.cgi?cid=1358256 (accessed Dec. 21, 2015), create date Jul. 11, 2005.
PubChem CID 1220560—National Center for Biotechnology Information, PubChem Compound Database; CID=1220560, http://pubchem.ncbi.nlm.nih.gov/summary/summary.cgi?cid=1220560 (accessed Dec. 21, 2015), create date Jul. 10, 2005.
PubChem CID 8582409—National Center for Biotechnology Information, PubChem Compound Database; CID=8582409, http://pubchem.ncbi.nlm.nih.gov/summary/summary.cgi?cid=8582409 (accessed Dec. 21, 2015), create date Jul. 30, 2006.

\* cited by examiner

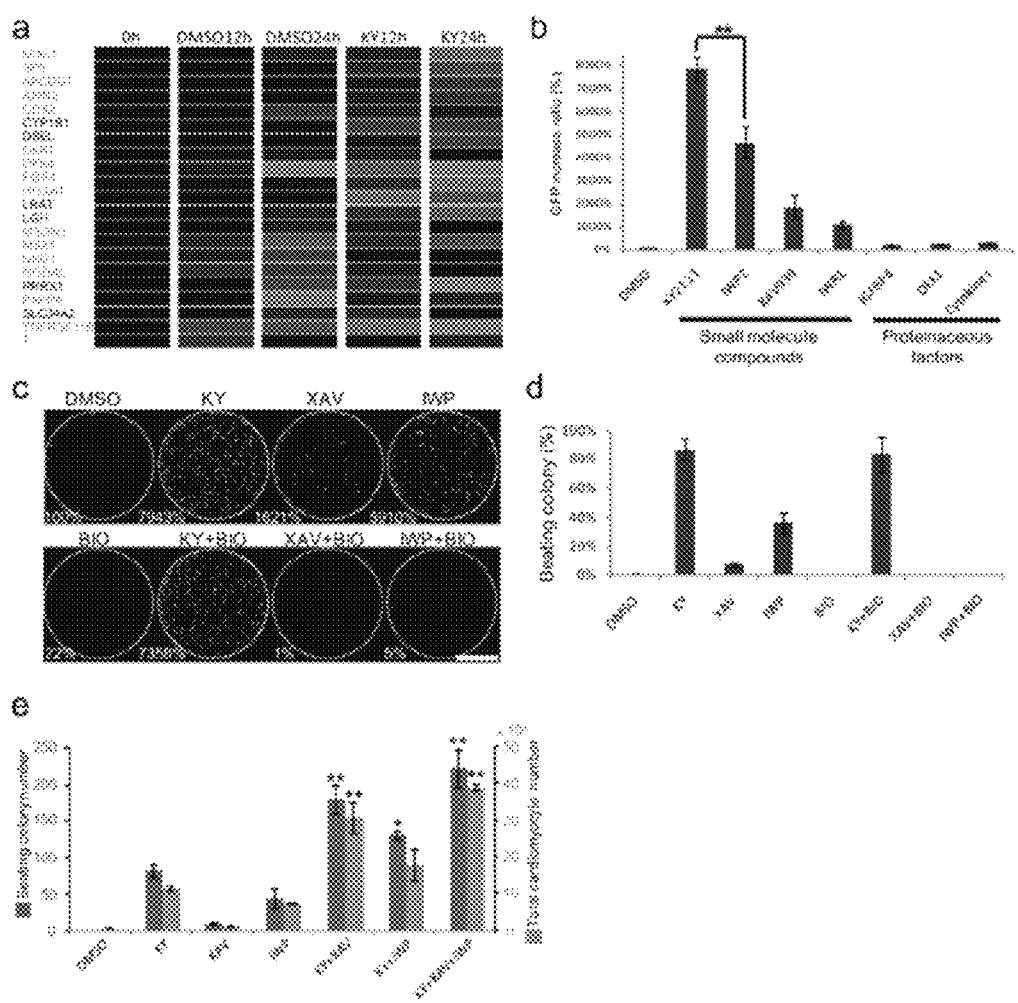

b c

Fig. 10
a
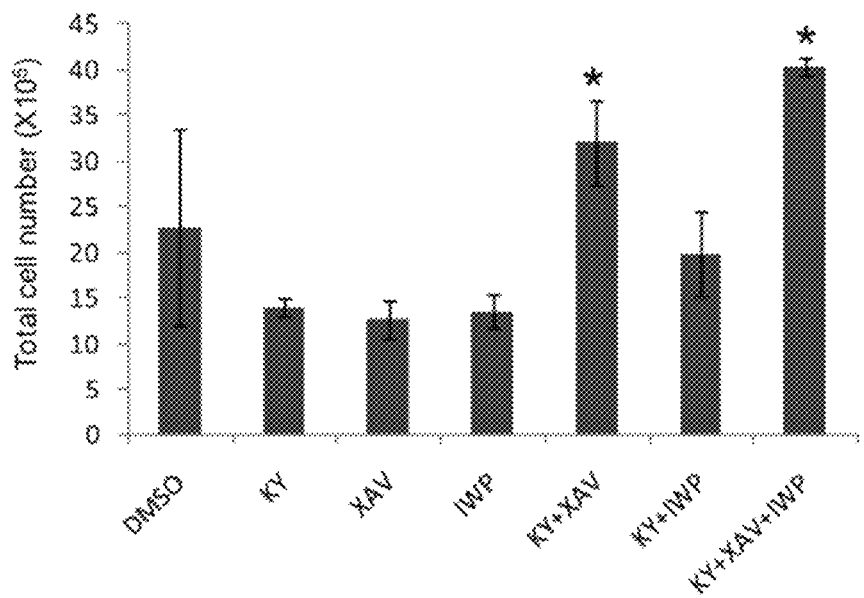
b
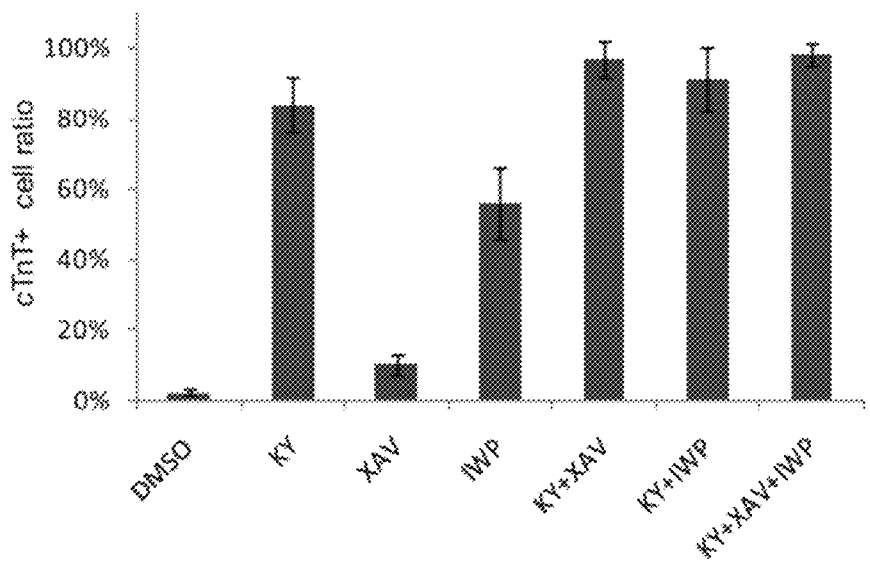

Fig. 11
a
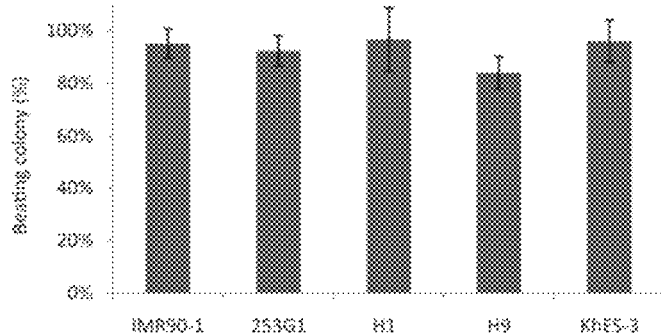
b
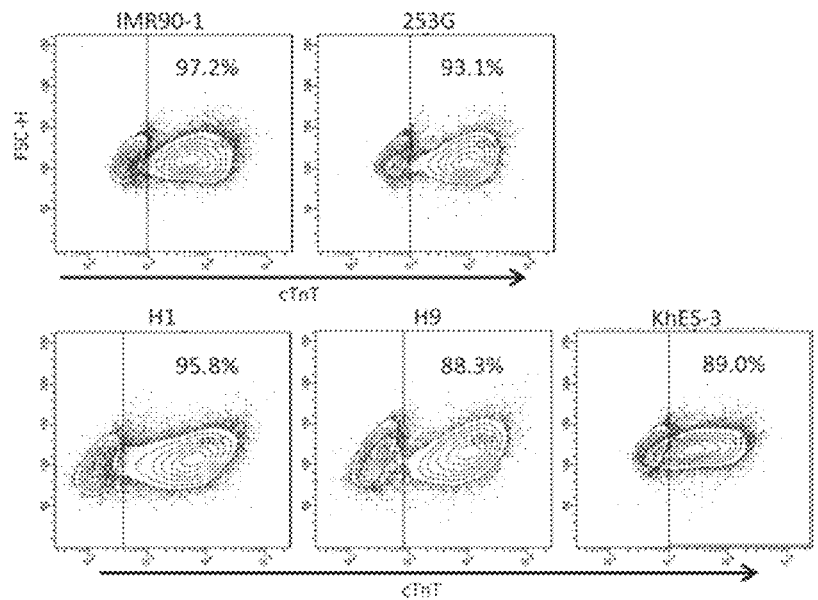
c
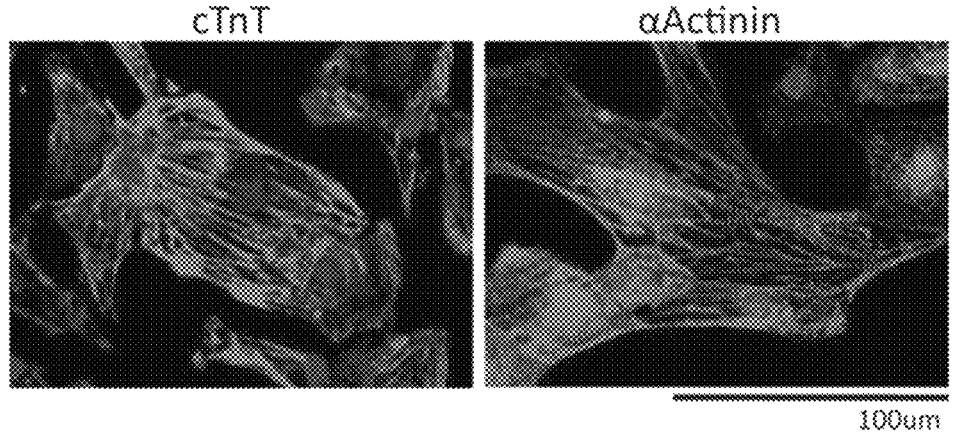

METHOD FOR INDUCING CARDIAC DIFFERENTIATION OF PLURIPOTENT STEM CELL

TECHNICAL FIELD

The present invention relates to a method for inducing cardiac differentiation of a pluripotent stem cell.

BACKGROUND

Human pluripotent stem cells (hPSCs), including embryonic stem cells (hESCs) and induced pluripotent stem cells (hiPSCs), can proliferate indefinitely in the undifferentiated state, and differentiate into many types of cells in human tissues, including the heart (Non-patent literatures 1-7). Therefore, hPSCs are potentially useful in cell-baaed therapies for heart disease. Efficient production of functional cardiac cells from hPSCs is required for cell-based therapy. The most common methods currently used are suspension culture of embryoid bodies with cytokines, such as DKK1, bFGF, Activin A, and EMP4, or adhesion co-culture with mouse END2 (visceral endoderm-like cells) (Non-patent literatures 13, and 15-17) However, these methods have low efficiencies (10-50% cardiomyocytes produced) (Non-patent literature 15), xeno-contamination is unavoidable with the use of animal cells or fetal bovine serum (FBS) (Non-patent literature 18), and use of recombinant cytokines is not cost-effective for large-scale production. Furthermore, a previous study showed that optimal cytokine concentrations for cardiac induction differ among individual hPSC lines (Non-patent literature 19), indicating the need for optimization procedures. A universal cardiac differentiation method that is independent of hPSC lines was recently reported, but it requires FBS and growth factors, such as bFGF and BMP4, for efficient differentiation (Non-patent literature 20).

Small molecules have great potential as substitutes for recombinant cytokines and unknown factors in FBS (Non-patent literature 21), and they are suitable for making defined media for large-scale culture. To date, small molecules have been used to activate or inhibit signaling pathways, such as WNT or TGF-β signaling (Non-patent literatures 22 and 23), or to regulate the expression of genes in place of transcription factors (Non-patent literatures 24 and 25). A number of small molecules have been examined or screened for promotion of differentiation: a BMP signaling inhibitor (Dorsomorphin), a p38MAPK signaling inhibitor (SB203580), a WNT signaling activator (BIO), and WNT signaling inhibitors (XAV939, IWR-1, IWP-1, and IWP-3) were reported to promote cardiac differentiation (Non-patent literatures 26-32). However, these treatments resulted in only 10-60% differentiation to cardiomyocytes, even under serum-containing conditions (Non-patent literatures 26-32). A small molecule that produces more efficient differentiation is needed for large-scale clinical applications.

SUMMARY

An object of the invention is to provide an efficient method for inducing cardiac differentiation of a pluripotent stem cell.

The invention provides a method for inducing cardiac differentiation of a pluripotent stem cell, which comprises the steps of
(1) culturing a pluripotent stem cell in a medium containing one or more WNT signaling activators, and
(2) culturing a cell produced in the step (1) in a medium containing one or more WNT signaling inhibitors.

The invention provides a kit for promoting cardiac differentiation comprising one or more WNT signaling activators and/or one or more WNT signaling inhibitors, wherein the kit is used for the aforementioned method.

According to the present invention, cardiac differentiation of a pluripotent stem cell is induced efficiently and at a low cost compared to known methods.

(a) Diagram of Small Molecule Screening. One hit compound was identified from the chemical of 9600 compounds (Non-patent literature 47), using human αMHC promoter-driven EGFP (enhanced green fluorescent protein) transgenic monkey ESCs and an HCA system.

(b) Effective Time Window of Hit Compound, N11474. Treatment on Days 4-8 was the most effective for cardiac differentiation, based on the ratio of GFP expression driven by human αMHC promoter. The expression level of the DMSO control is 100%. The treatment during Days 0-4 completely suppressed GFP expression. The experiment was run twice.

(c, d) Structure-activity relationships of N11474 and related compounds, and their promotion of cardiac differentiation. (c) Chemical formulas of N11474 and KY02111. (d) GFP expression level induced by N11474 and related compounds. Top graph shows GFP increase ratio. White dots in the whole well images (bottom photos) indicated colonies with GFP signals (scale bar indicates 10 mm). The length of carbon chain that connects the benzothiazole ring to the dimethoxyphenyl ring was important for inducing GFP expression: compounds having 2or 3 carbons (KY02111 or KY02114) induced the highest levels. The experiment was run three times.

(e) Generality of KY02111 effect on PSC lines. hESC lines (KhES-1 and KhES-3), monkey ESC line (CMK6.4), mouse ESC line (R1), and hiPSC lines (IMR90-1, IMR90-4, 253G1, and RCHIPC0003) were differentiated into cardiomyocytes by treatment with KY02111. The ratio of beating colonies per all of colonies on culture dish increased 70-90% for all PSC lines (mean±SEM, n=2).

Figure 2:
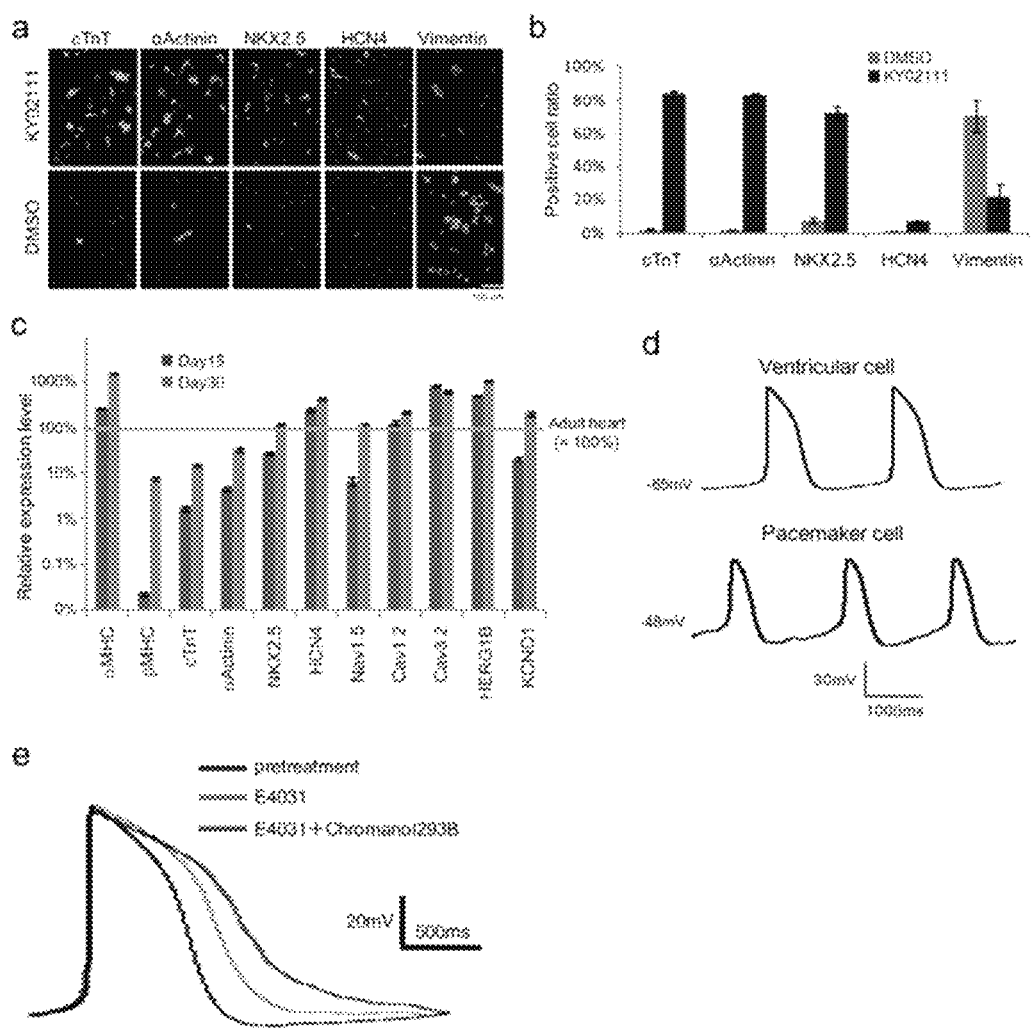

FIG. 2. Characterization of cardiomyocytes derived from hPSCs treated with KY02111.

(a, b) KY02111 promoted the expression level of cardiac markers. (a) IMR90-1 hiPSCs were treated with KY02111 or DMSO, and then cardiac markers (cTnT, αActinin, and NKX2.5), pacemaker marker, HCN4, and fibroblast marker, Vimentin, were detected. The upper and lower images are cells treated with KY02111 or DMSO, respectively (scale bar indicates 100 μm). (b) Approximately 80% or 16% of KY02111-treated cells, and 2% or 0.8% of control cells, were positive for cardiac markers or HCN4, respectively. The Vimentin-positive ratio was 20% and 70% in KY02111 and DMSO, respectively (mean±SEM, n=3).

(c) qPCR gene expression analysis of KY02111-induced cardiomyocytes. Total RNA was extracted from differentiated cells on Days 15 (left bar) and 30 (right bar) of cardiac differentiation. Cardiac marker genes (αMHC, βMHC, cTnT, αActinin, and NKX2.5) and channel genes (HCN4, Nav1.5, Cav1.2, Cav3.2, HERG1b, and KCNQ1) were highly expressed in KY02111-induced cardiomyocytes. Almost all genes were up-regulated at Day 30, and their gene expression levels were nearly equal to the gene expression levels of adult heart tissue, which was considered to be 100% (mean±SEM, n=3). All primers used in qPCR are shown in Table 1.

(d, e) Functionality of KY02111-induced cardiomyocytes (KY-CMs). (d) Spontaneous ventricular-like or pacemaker-like action potential (AP) in patch clamp recordings from KY02111-induced cardiomyocytes. (e) Prolongation of action potential duration induced by 100 nM E4031 (HERG channel blocker) and 4 μM chromanol293B (KCNQ1 channel blocker). These results indicate that KY-CMs are electrically and pharmacologically functional.

Figures 1, 9:
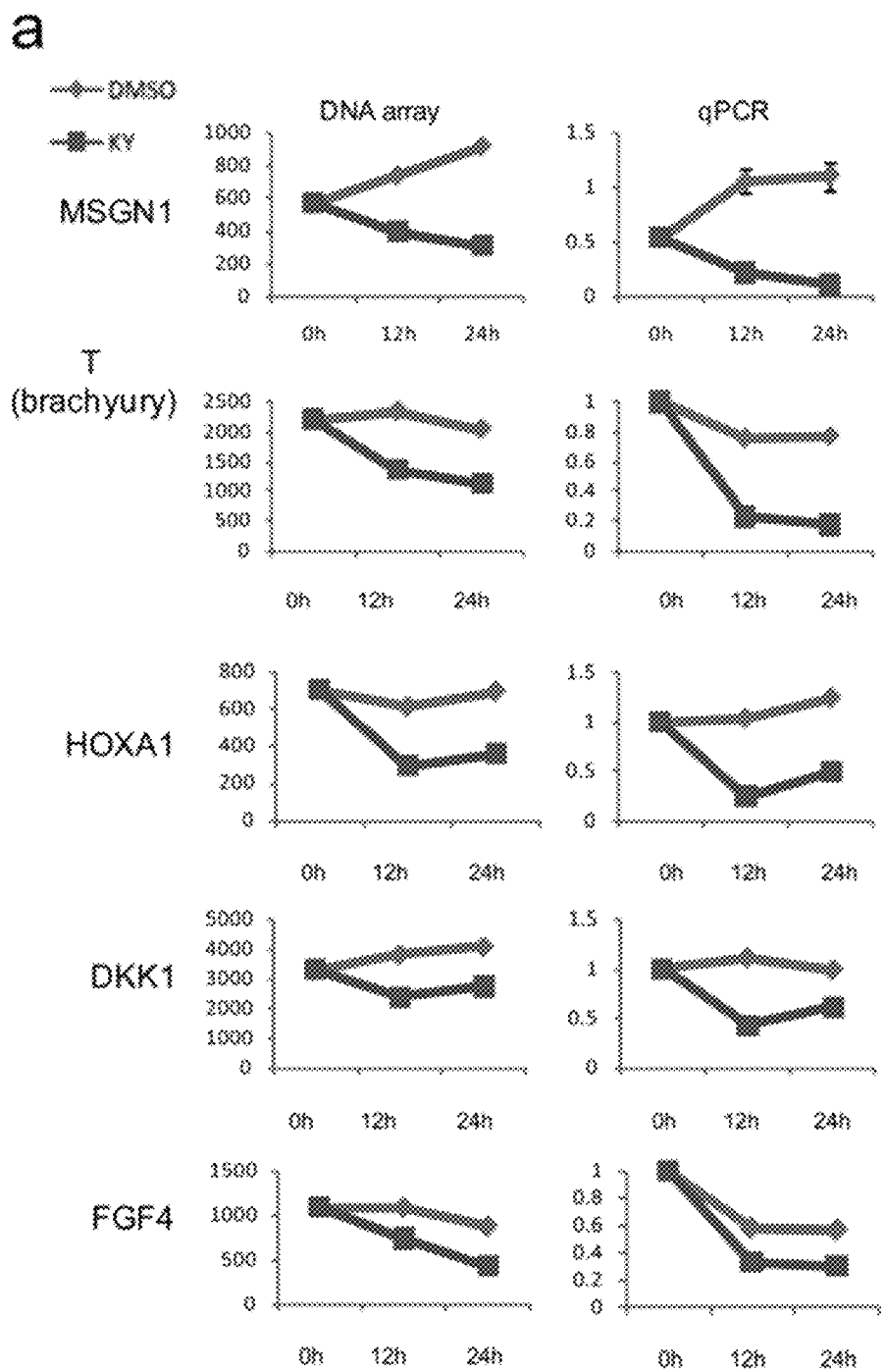
Figure 9:
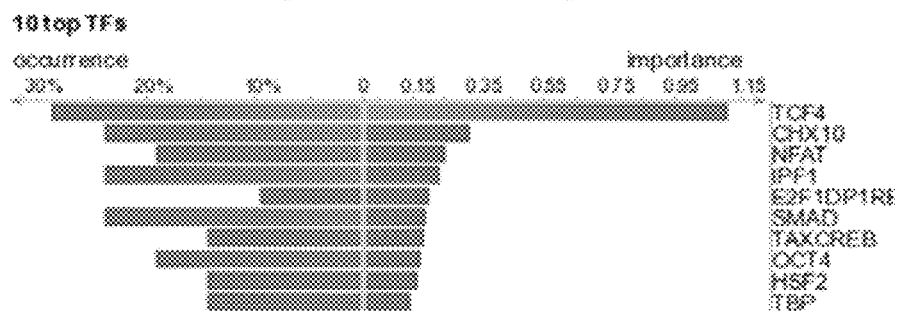
Figure 2:
Figures 3, 9:
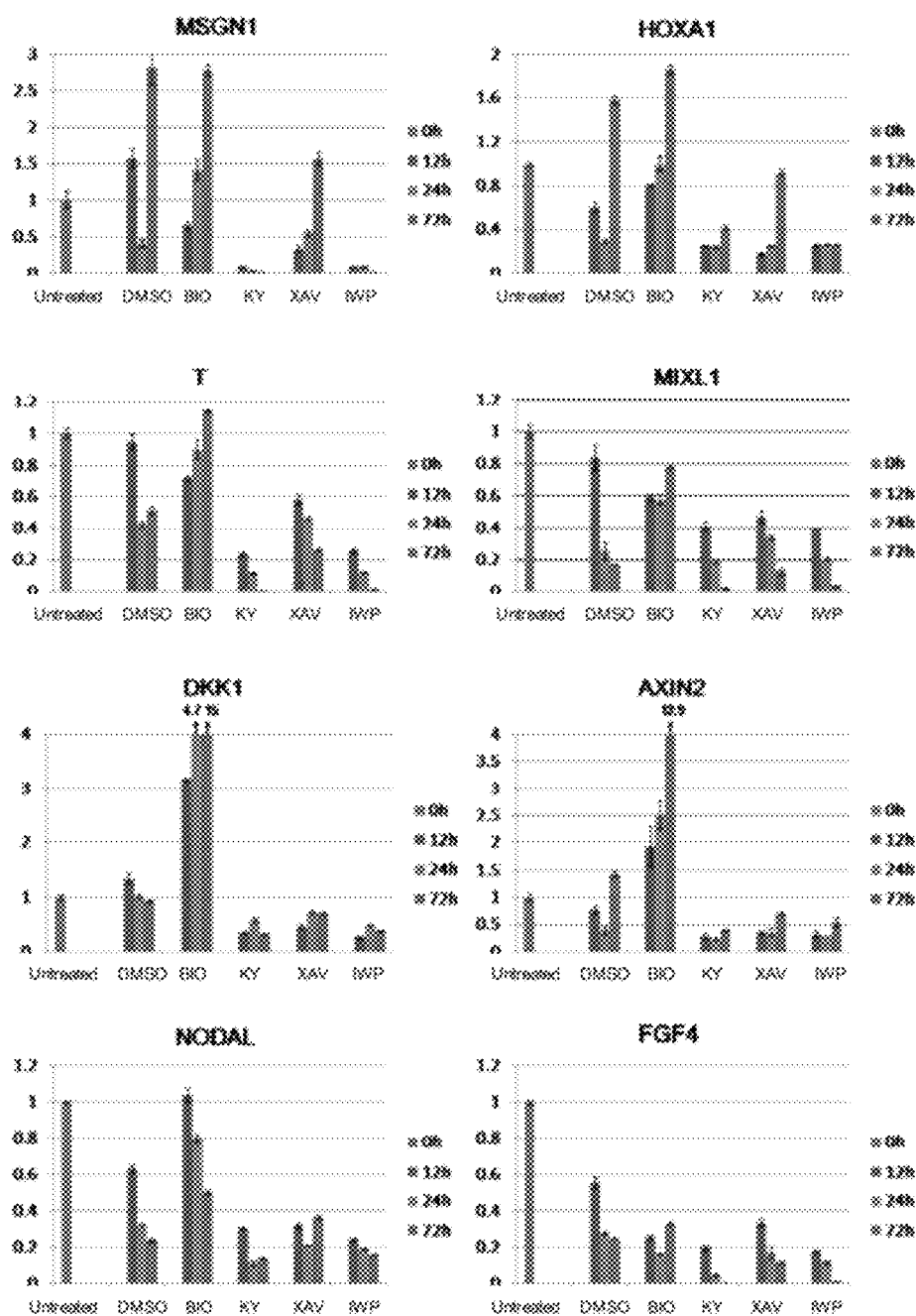
Figures 4, 9:
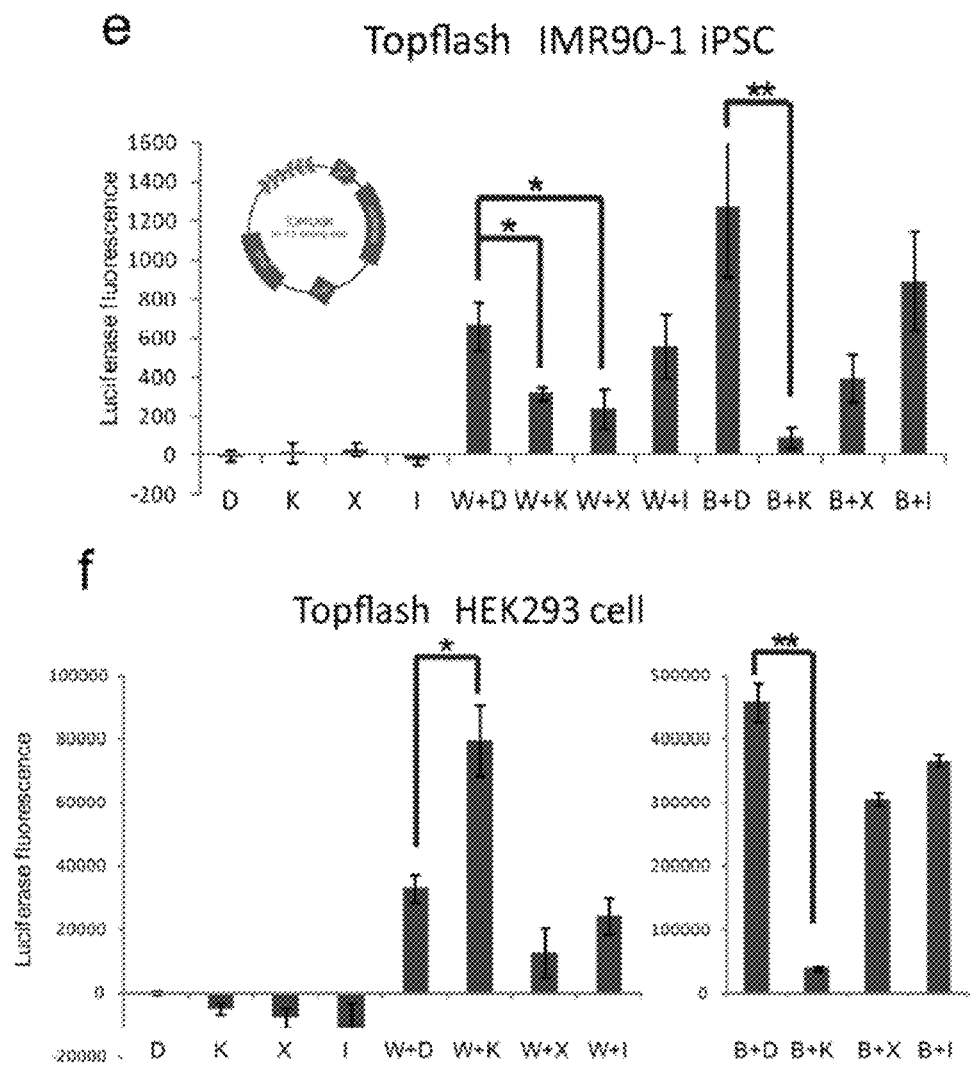

FIG. 3. KY02111 and other WNT inhibitors synergistically promote cardiac differentiation through inhibition of WNT signaling.

(a) Heatmap of Down-Regulated Genes. IMR90-1 hiPSCs were treated with KY02111 or DMSO for 12 or 24 h (KY12h, KY24h, DMSO12h, or DMSO24h), and 26 genes were identified. Twenty-two down-regulated genes were used to generate the heatmap. Four up-regulated genes are shown in Table 2. WNT-signaling target gene are described in Table 2.

(b) Comparison of cardiac differentiation promoting activity among chemical and proteinaceous WNT inhibitors (mean±SEM, n=4; **Student's t-test, P=0.009). The activity was measured using monkey ESCs with EGFP gene driven by human αMHC promoter. The activity level of the DMSO control treatment was considered to be 100%. The small molecule WNT inhibitors were KY02111 (10 μM), IWP-2 (10 μM), XAV939 (10 μM), and IWR-1 (10 μM). The proteinaceous factors were IGFBP4 (1 μg ml$^{-1}$), Dkk1 (300 ng ml$^{-1}$), and a mixture of bFGF, BMP4, VEGF, DKK1, and Activin A (cytokines) (Non-patent literature 16). The concentrations of all inhibitors were optimized for cardiac differentiation (data not shown).

(c, d) A GSK3β inhibitor did not abolish the effect of KY02111 on cardiac differentiation. Colonies with GFP signal driven by human αMHC promoter were produced using KY02111 (KY), XAV939 (XAV), IWP-2 (IWP) treatment, with or without 5 μM BIO (a GSK3β inhibitor). (c) Images of the GFP signal (white dots) in whole wells. Numbers at bottom left of each image indicates the increase in GFP signal ratio (DMSO=100%). (d) Proportions of beating colonies (mean±SEM, n=3), showing that BIO did not cancel promotion of cardiac differentiation by KY02111, but did completely inhibit activities of XAV939 and IWP-2.

(e) Synergistic effects of KY02111 with XAV939, IWP-2, or both. On Day 0 of differentiation, 6×10$^6$ IMR90-1 hiPSC cells per well were added to a 6-well plate. Left bars show the numbers of beating cardiac colonies induced by KY02111 (KY), XAV939 (XAV), IWP-2 (IWP), KY+XAV, KY+IWP, and KY+XAV+IWP. Right bars show the total number of cardiomyocytes, calculated by multiplying total cell numbers of all colonies by the ratio of cTnT-positive cells (see FIG. 10a, b). Mean±SEM, n=4, *P<0.05, **P<0.001 for Student's t-tests comparing each treatment to KY02111 alone.

Figure 4:
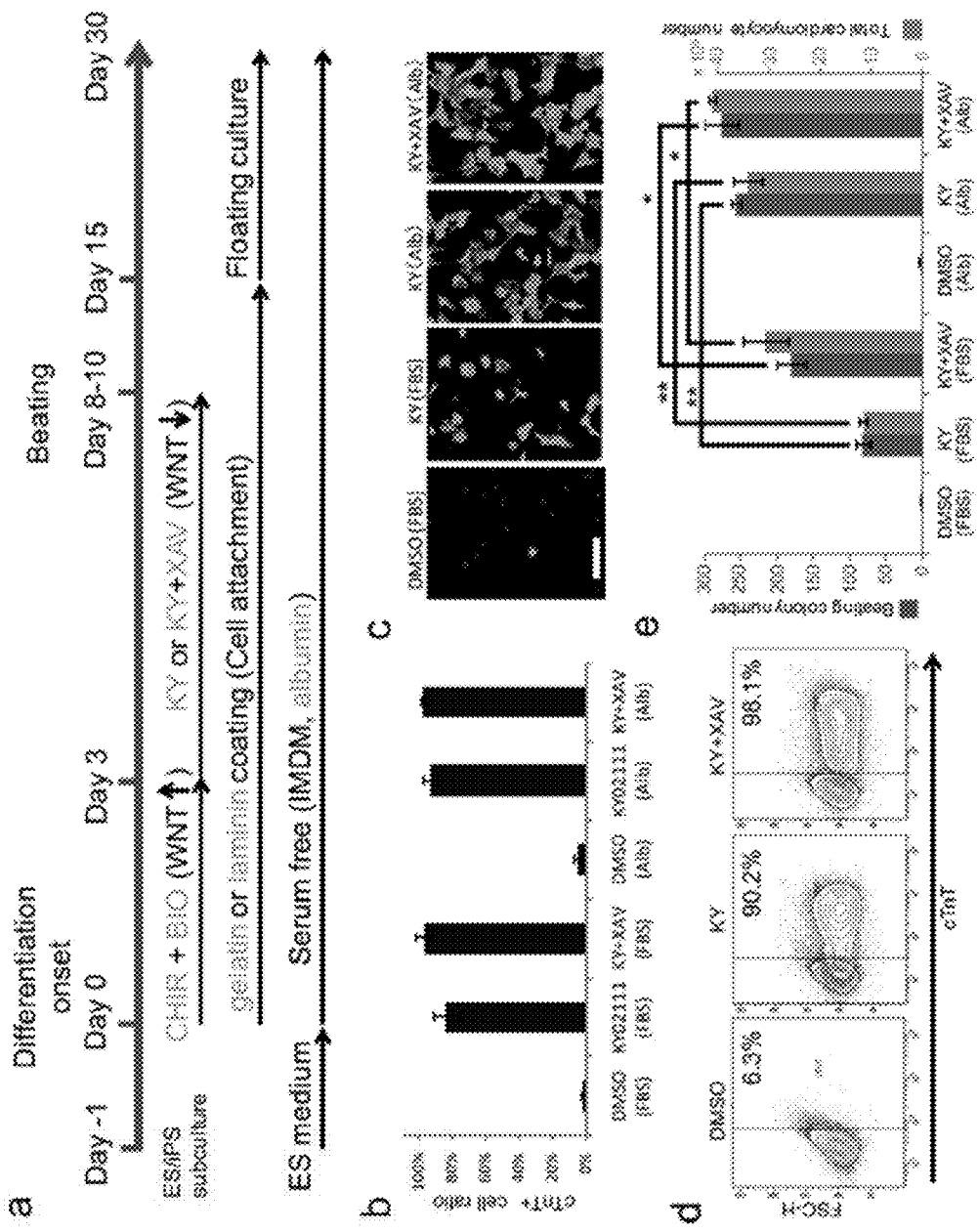

FIG. 4. Cardiac differentiation in serum-free and defined medium using small molecules that regulate WNT signaling.

(a) A scheme of cardiac differentiation using WNT signaling regulators. In the early phase of differentiation (Days 0-3), precultured hPSC aggregates were cultured in serum-free, IMDM-based medium, including 0.4-2% albumin and GSK3β inhibitors (2 μM BIO and 5 μM CHIR99021) on gelatin or laminin211-coated dishes. In the middle phase (Days 3-9), cells were cultured in defined medium with 10 μM KY02111, or 10 μM KY02111 and 2 μM XAV939. Beating cardiac colonies usually emerged on Day 9. In the late phase (Days 9-30), cardiac colonies were kept in defined medium without WNT signaling regulators by floating culture, as previously described (Non-patent literature 33).

(b) Differentiation efficiency under serum-free and serum-containing conditions. Cardiac differentiation was carried out according to FIG. 4a, using medium with serum (FBS) or 1-2% BSA (Alb). The proportion of cTnT-positive cells were measured by Metamorph software.

(c) cTnT immunostaining of differentiated cells under serum-containing (FBS) and serum-free (Alb) conditions. Scale bar indicates 100 μm.

(d) Representative flow cytometry data for cTnT-positive cells induced by control DMSO, KY02111 (KY), or KY02111+XAV939 (KY+XAV) in albumin-containing medium. 30,000 cells were measured in each sample by FACSCantoII (BD Biosciences).

(e) The number of beating colonies (left bars) and total number of cardiomyocytes (right bars) in serum-free and defined culture conditions. On Day 0 of differentiation, 6×10$^6$ IMR90-1 hiPSC cells per well were added to a 6-well plate. Right bars show cardiomyocyte numbers in each well, calculated by multiplying total cell numbers of all colonies by the ratio of cTnT-positive cells. Both the number of beating colonies and the total number of cardiomyocytes induced by KY02111 or KY+XAV increased more in defined medium (Alb) than in serum-containing medium (FBS). Mean±SEM, n=4; *P<0.05, **P<0.001 for Student's t-tests.

Figure 5:
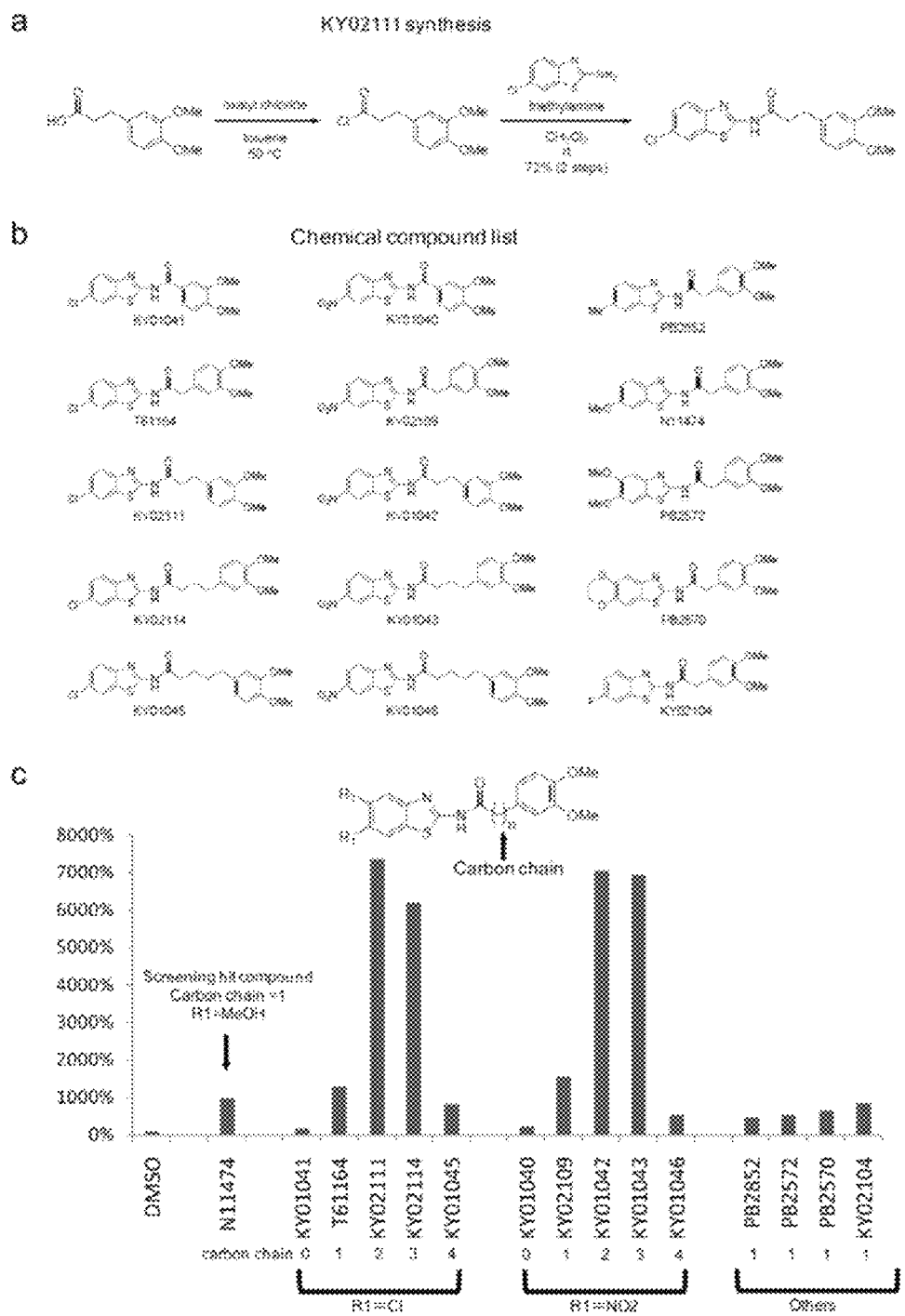

FIG. 5. KY02111 and relative compounds.

(a) Synthetic scheme for KY02111. A similar synthetic method was used to generate other relative compounds.

(b) Chemical structures of KY02111 relative compounds which had cardiac differentiation promoting activities.

(c) Cardiac differentiation activities (αMHC-promoter driven GFP increase ratios of monkey ESCs, DMSO=100%) of KY02111 relative compounds listed in (b). The compounds of carbon chain number 2 or 3 had stronger activities than the compounds of carbon chain number 0, 1 or 4. Chloride and nitro group were better for R1 group of benzothiazole ring than methyl, hydroxymethyl, and fluorine group.

Figure 6:
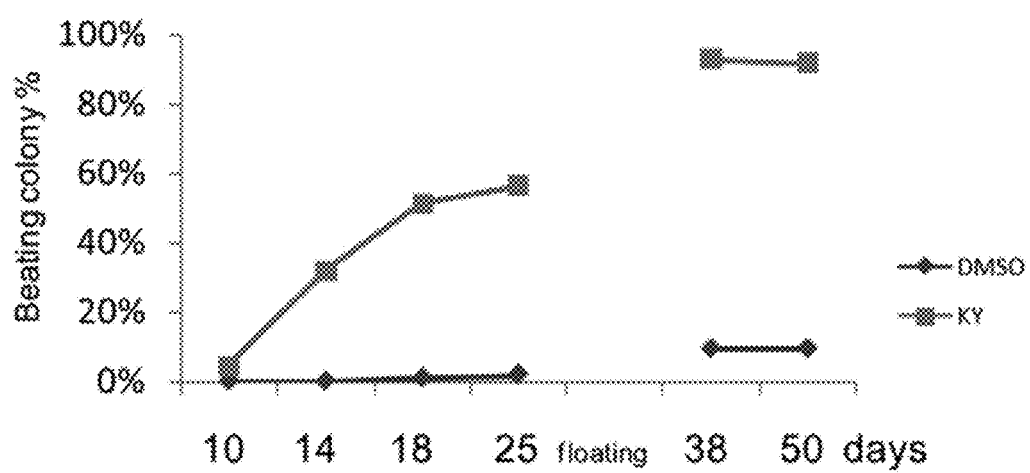

FIG. 6. Time course of cardiac differentiation induced by KY02111.

The beating colony ratio of hiPSCs (IMR90-1) increased from days 10 to 38 during cardiac differentiation. Beating started at about day 10. On day 30, cardiac colonies on the dished were transferred to floating culture as described in "1. Methods" in the examples.

Figure 7:
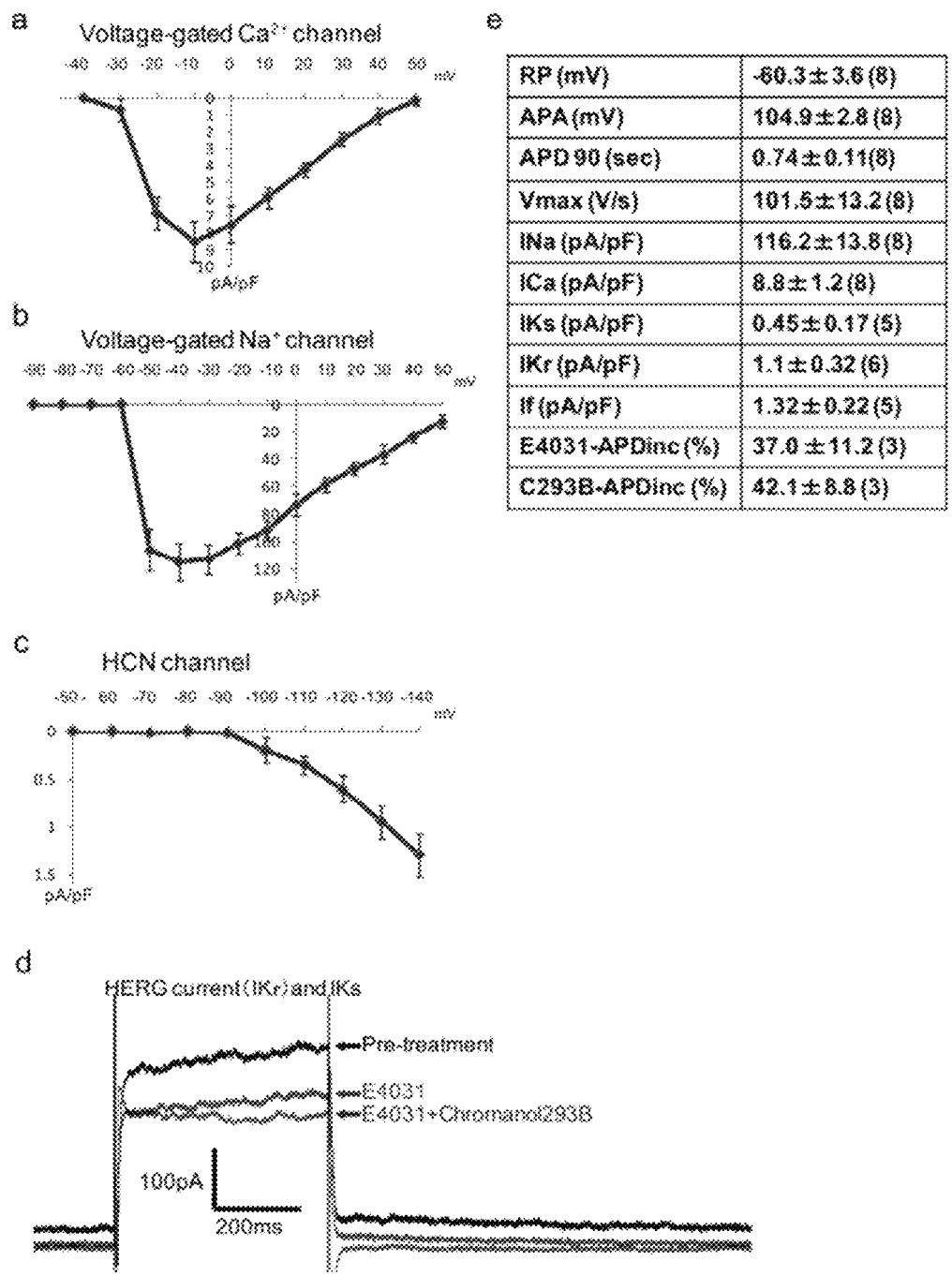

FIG. 7. Patch clamp recordings of cardiomyocytes induced by KY02111.

(a) Current-voltage (I-V) relationship of Voltage-gated Ca2+ channel currents of KY02111 induced cardiomyocytes (KY-CMs) (n=8, mean±SEM).

(b) Current-voltage (I-V) relationship of Voltage-gated Na+ channel currents of KY-CMs (n=8, mean±SEM).

(c) Current-voltage (I-V) relationship of HCN channels currents of KY-CMs (n=5, mean±SEM).

(d) A HERG channel current (IKr) and KCNQ1 current (IKs) of KY-CMs. Holding potential, −40 mV; depolarizing test pulses, −40 to +40 mV for 500 msec. 3 traces were merged, pre-treatment (top), after HERG channel blocker E4031 treatment (middle), and after KCNQ1 channel blocker chromanol293B treatment (bottom). Inhibitions of the IKr and IKs currents due to E4031 and chromanol293B were clearly detected in KY-CMs.

(e) Average properties of action potentials and ion channel currents of KY-CMs. RP: Resting potential. APA: Action potential amplitude. APD90: Action potential duration at 90% repolarization. Vmax: Maximum upstroke velocity. INa: Voltage-gated Na+ channel currents at depolarizing from −90 to 40 mV. ICa: Voltage-gated Ca2+ channel currents at depolarizing from −40 to −10 mV. IKs: Voltage-gated K+ channel currents after 500 ms depolarizing pulses from −40 to 40 mV suppressed by chromanol293B. IKr: Voltage-gated K+ channel currents after 500 ms depolarizing pulses from −40 to 40 mV suppressed by E4031. If: HCN channel currents after 500 ms hyperpolarizing pulses from −50 to −140 mV suppressed by zatebradine. E4031-APDinc: APD90 increase ratio induced by E4031. C293B-APDinc: APD90 increase ratio induced by chromanol293B.

Figure 8:
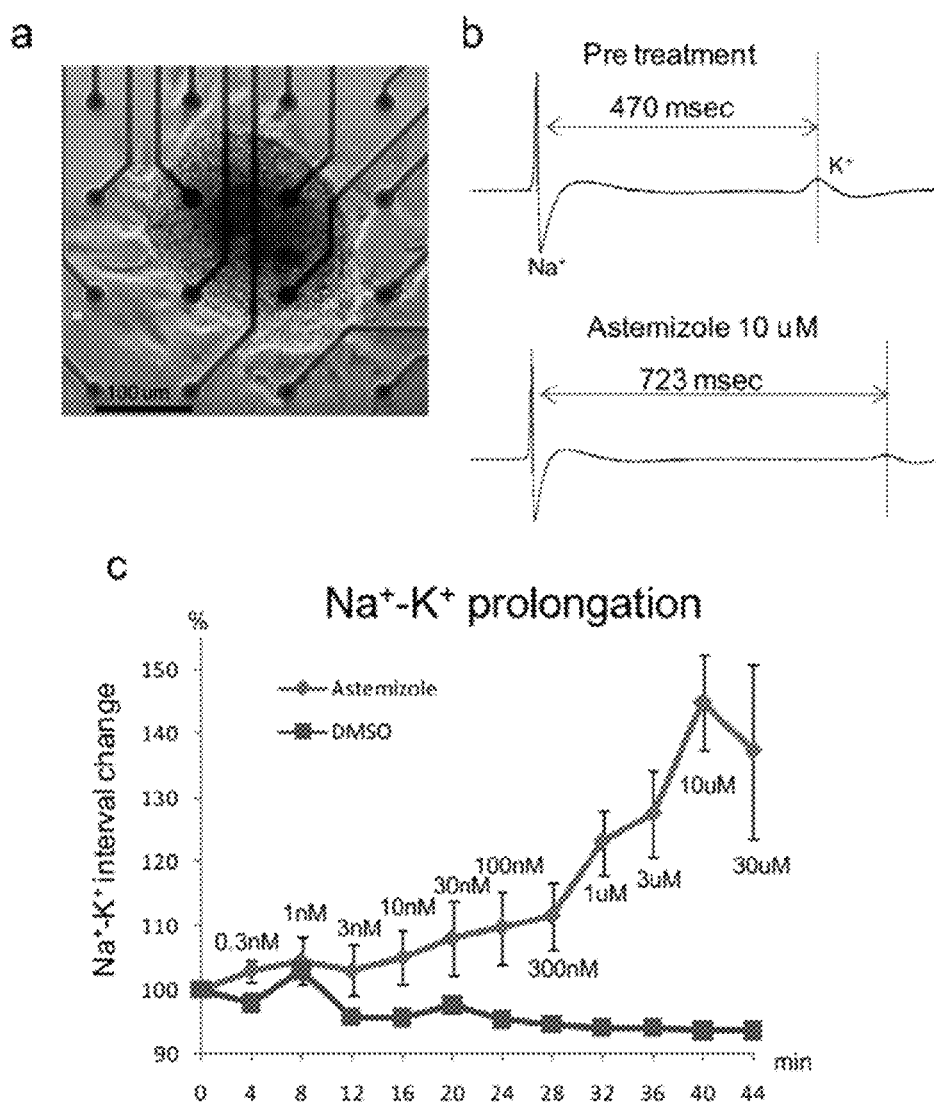

FIG. 8. QT interval prolongation test using KY-CMs.
(a) Single KY-CM colony on a microelectrode array (MEA) dish.
(b) ECG-like waves emitted from a KY-CM colony. Top: A pre-treatment wave form. Bottom: A wave form after 10 µM astemizole treatment. Na+—K+ wave peak interval was prolonged by astemizole. Astemizole is an antihistamine drug, but it was reported to block HERG channel (Non-patent literature 34).
(c) Na+—K+ interval, prolongation graph. Astemizole was added in a dose-dependent manner every 4 minutes. Na+—K+ interval didn't change in 0.1% DMSO treatment as control condition.

Figure 1:
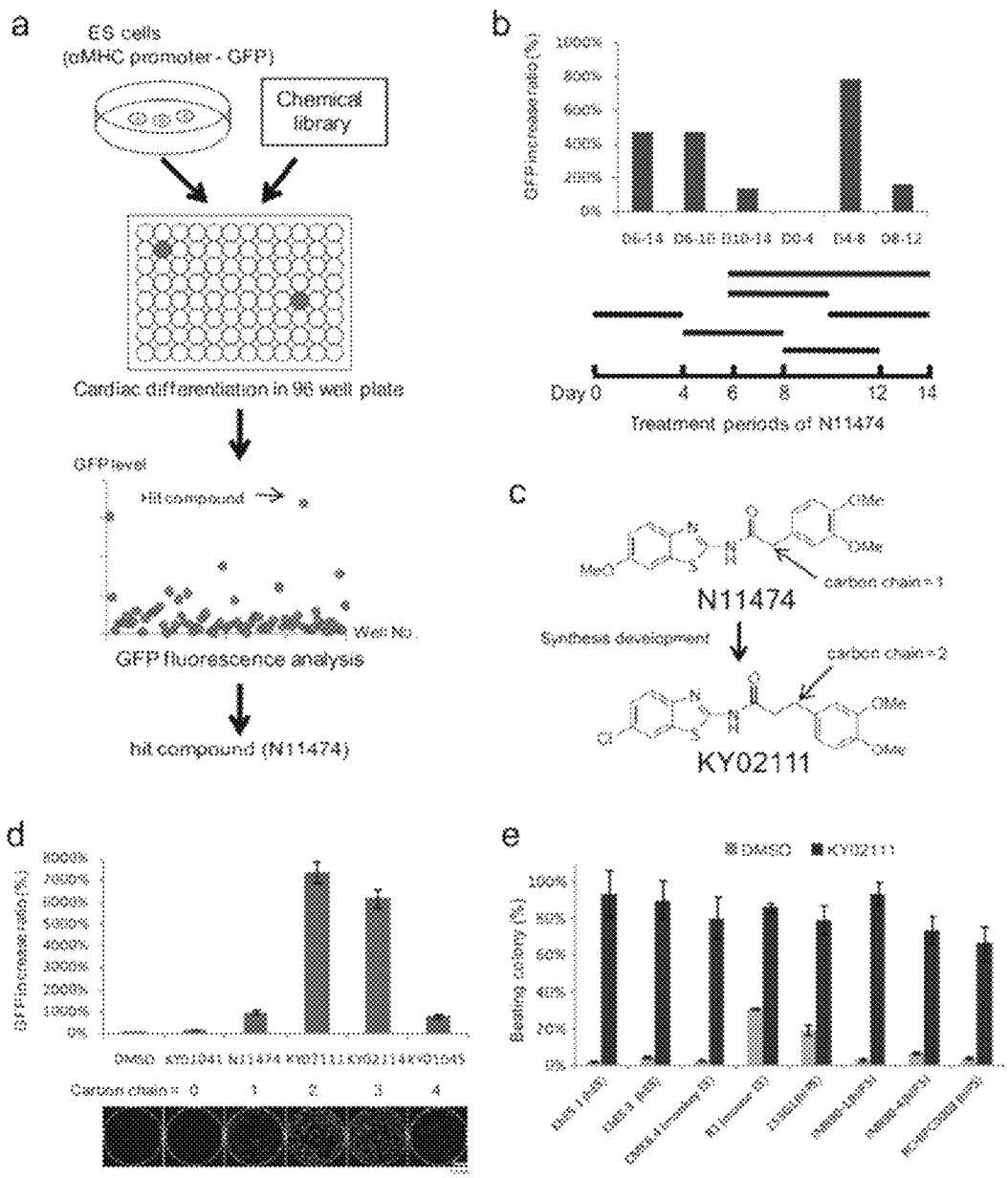
FIG. 1. Identification and characterization of small molecules that promote cardiac differentiation.

FIG. 9-1. Gene expression profiles and TCF reporter assay by KY02111 and WNT signaling regulators (1).
(a) The validation of WNT target genes identified by the microarray experiment of KY02111-treated IMR90-1 hiPSCs. The gene expression pattern by qPCR analysis was similar to that of microarray data in all tested genes.

FIG. 9-2. Gene expression profiles and TCF reporter assay by KY02111 and WNT signaling regulators (2).
(b, c) DIRE (Distant Regulating Elements of co-regulated genes) analysis (Non-patent literature 35) of genes down-regulated by KY02111 treatment. All 22 genes (b) or the most down-regulated 10 genes (c) at 12 h after KY02111 treatment were analyzed. Output data showed that more reasonable transcription factors were LEF1 and TCF4, which are canonical WNT signaling effectors.

FIG. 9-3. Gene expression profiles and TCF reporter assay by KY02111 and WNT signaling regulators (3).
(d) The gene expression analysis of KY02111, XAV939, IWP-2, or BIO-treated IMR90-1 hiPSCs by qPCR. Total RNAs were extracted at 12, 24 and 72 h after treatments. The expression levels of all tested genes were suppressed by WNT signaling inhibitors (XAV939 and IWP-2) and KY02111. A WNT signaling activator BIO tended to augment these gene expression levels.

FIG. 9-4. Gene expression profiles and TCF reporter assay by KY02111 and WNT signaling regulators (4).
(e) TCF reporter-luciferase assay of KY02111 (K), XAV939 (X), IWP-2 (I), and DMSO control (D) using TOPflash-plasmid transfected hiPSCs (IMR90-1). Wnt3a (W) or BIO (B) were added to elevate WNT signaling and TCF promoter activity. KY02111 and XAV939 inhibited TCP promoter activities by Wnt3a and BIO. IWP-2 didn't inhibit TCF promoter activities, probably because IWP-2 is an inhibitor of WNT ligand secretion. n=14, mean±SEM, *P<0.05, **P<0.01 by an unpaired two-tailed Student's t-test.
(f) TCP reporter assay of KY02111 in HEK293 cells. KY02111 inhibited TCF promoter activity by BIO, but KY02111 further augmented TCF promoter activity by Wnt3a in HEK293 cells. n=4, mean±SEM, *P<0.05, **P<0.01 by an unpaired two-tailed Student's t-test.

FIG. 10. Synergistic effects on total cell number and cardiomyocyte ratio of KY02111 with XAV939, IWP-2, and both.
(a) Total numbers of differentiated cells in single well of a 6 multi-well plate.
(b) cTnT-positive cardiomyocytes ratio. IMR90-1 hiPSCs were treated with KY02111 (KY), XAV939 (XAV), IWP-2 (IWP), KY+XAV, KY+IWP, or KY+XAV+IWP as described in "1. Methods" in the examples. Total cell numbers were measured on Day 14 of cardiac differentiation using NucleoCounter (Chemometec). The cTnT-positive cardiomyocytes was examined as described in "1. Methods" in the examples. Six million cells of IMR90-1 hiPSCs were used in one well of a 6-well plate at the Day 0 of differentiation. n=4, mean±SEM, *P<0.001, compared to KY02111 alone.

FIG. 11. Robust cardiac differentiation in cytokine-free, serum-free and xeno-free defined condition using small molecules regulating WNT signaling.
(a) hESC lines (H1, H9 and KhES-3) and hiPSC lines (IMR90-1 and 253G1) were highly efficiently differentiated into cardiomyocytes by BIO+CHIR99021 treatment in the early phase and KY02111+XAV939 treatment in later phase. 0.4% human serum albumin and human laminin211 were used as shown in FIG. 4a. Cardiac beating colony ratio (beating colonies per all of colonies on a culture dish) were 85-95% in all hPSC lines. n=3, mean±SEM.
(b) Representative flow cytometry data of cTnT-positive cells generated from each hPSCs line. 30,000 cells were measured in each sample by FACSCantoII (BD Biosciences).
(c) The immunostaining of cTnT and αActinin in cardiomyocytes derived from IMR90-1 hiPSCs under xeno-free and cytokine-free condition. Scale bar, 100 µm. Sarcomere structures were clearly detected.

DESCRIPTION OF EMBODIMENTS

The term "pluripotent stem cell" (also referred to as "PSC") herein used refers to a cell having an ability to differentiate any type of cell constituting an adult body (pluripotency) and self-renewal capacity which is an ability to maintain the pluripotency during cell division. The "pluripotent stem cell" includes an embryonic stem cell (an ES cell, also referred to as "ESC"), an embryonic germ cell (an EG cell), and an induced pluripotent stem cell (an iPS cells, also referred to as "iPSC"). The "pluripotent stem cell" may be a cell of any species with no limitation, and preferably a mammalian cell, and more preferably a rodent or primate cell. The present invention is particularly suitable for a monkey or human pluripotent stem cell.

An ES cell is a pluripotent stem cell derived from early embryo and may be established from inner cell mass of a blastocyst or post-implantation epiblast in early embryo. Examples of the ES cell include those described in the following references: human (Thomson J. A. et al., Science 282: 1145-1147 (1998), Biochem Biophys Res Commun. 345 (3), 926-32 (2006); primates such as rhesus macaque and marmoset (Thomson J. A. et al., Proc. Natl. Acad. Sci. USA 92: 7844-7848 (1995); Thomson J. A. et al., Biol. Reprod. 55: 254-259 (1996); rabbit (National Publication of International Patent Application No. 2000-508919); hamster (Doetshman T. et al., Dev. Biol. 127: 224-227 (1988)), hog (Evans M. J. et al., Theriogenology 33:125128 (1990); Piedrahita J. A. et al., Theriogenology 34: 879-891 (1990); Notarianni E. et al., J. Reprod. Fert. 40: 51-56 (1990); Talbot N. C. et al., Cell. Dev. Biol. 29A: 546-554 (1993)), sheep (Notarianni E. et al., J. Reprod. Fert. Suppl. 43: 255-260 (1991)), cow (Evans M. J. et al., Theriogenology 33: 125-128 (1990); Saito S. et al., Roux. Arch. Dev. Biol. 201: 134-141 (1992)), and mink (Sukoyan M. A. et al., Mol. Reorod. Dev. 33: 418-431 (1993)) (these references are herein incorporated by reference).

An EG cell is a pluripotent stem cell derived from a primordial germ cell, and examples include a human EG cell (Shamblott, et al., Proc. Natl. Acad. Sci USA 95:13726-13731 (1998)) (the reference is herein incorporated by reference.).

The term "iPS cell" herein used refers to a pluripotent stem cell induced from a cell other than a pluripotent stem cell such as a somatic cell and a tissue stem cell. Methods for preparing the iPS cell are described in the following references, for example: WO2007/069666, WO2009/006930, WO2009/006997, WO2009/007852, WO2008/118820, Cell Stem Cell 3 (5): 568-574 (2008), Cell Stem Cell 4 (5): 381-334 (2009), Nature 454: 646-650 (2008), Cell 136 (3): 411-419 (2009), Nature Biotechnology 26: 1269-1275 (2008), Cell Stem Cell 3: 475-479 (2008), Nature Cell Biology 11: 197-203 (2009), Cell 133 (2): 250-264 (2008), Cell 131 (5): 861-72 (2007), Science 318 (5858): 1917-20 (2007) (those references are herein incorporated by reference.). However, a cell prepared by any method is included in the "iPS cell" of the present invention as long as it is a pluripotent stem cell which has been induced artificially.

The "WNT signaling activator" as used herein refers to a substance which activates the WNT signaling pathway. Examples of the WNT signaling activator include a GSK3β inhibitor such as BIO or CHIR99021. In the method of the invention, more than two, for example 2, 3, or 4 WNT signaling activators may be used in combination.

The "WNT signaling inhibitor" an used herein refers to a substance which inhibits the WNT signaling pathway. Examples of the WNT signaling inhibitor include the compound of formula (I) or a salt thereof as described below, compounds such as IWP2, XAV939, and IWR1, and proteins such as IGFBP4 and Dkk1. Preferably, the WNT signaling inhibitor used in the invention is a compound. In the method of the invention, more than two, for example 2, 3, or 4 WNT signaling inhibitors may be used in combination.

A preferred WNT signaling inhibitor is a compound represented by Formula (I):

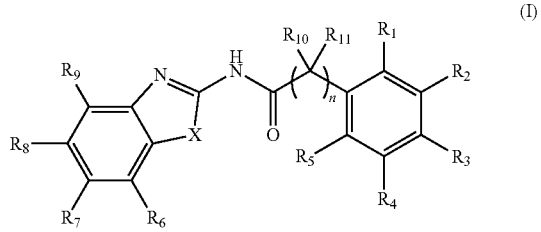

wherein $R_1$ to $R_5$ are each independently a hydrogen atom; a halogen atom; a hydroxyl group; a linear or branched alkoxy group having 1 to 5 carbon atoms; a linear or branched alkyl group having 1 to 5 carbon atoms which is unsubstituted or substituted with a halogen atom; or a group $—NR_{12}R_{13}$, wherein $R_{12}$ and $R_{13}$ are each independently a hydrogen atom, an oxygen atom, or a linear or branched alkyl group having 1 to 5 carbon atoms which is unsubstituted or substituted with a halogen atom; wherein two adjacent groups among $R_1$ to $R_5$ may join together to form $—O—CH_2—O—$ or $—O—(CH_2)_2—O—$, $R_6$ to $R_9$ are each independently a hydrogen atom; a halogen atom; a hydroxyl group; a linear or branched alkoxy group having 1 to 5 carbon atoms; a linear or branched alkoxy group having 1 to 5 carbon atoms which is substituted with a group $—C(O)A$, wherein A is a saturated or unsaturated 5- or 6-membered ring which is unsubstituted or substituted with a linear or branched alkyl group having 1 to 5 carbon atoms and the ring may contain 1 or 2 atoms independently selected from a nitrogen atom, an oxygen atom and a sulfur atom; a linear or branched alkyl group having 1 to 5 carbon atoms which is unsubstituted or substituted with a halogen atom; or a group $—NR_{12}R_{13}$, wherein $R_{12}$ and $R_{13}$ are each independently a hydrogen atom, an oxygen atom, or a linear or branched alkyl group having 1 to 5 carbon atoms which is unsubstituted or substituted with a halogen atom; wherein two adjacent, groups among $R_6$ to $R_9$ may join together to form $—O—CH_2—O—$ or $—O—(CH_2)_2—O—$, $R_{10}$ to $R_{11}$ are each independently a hydrogen atom; or a linear or branched alkyl group having 1 to 5 carbon atoms, X is $—CR_{14}$, wherein $R_{14}$ is a hydrogen atom, a halogen atom, a hydroxyl group, a linear or branched alkoxy group having 1 to 5 carbon atoms, or a linear or branched alkyl group having 1 to 5 carbon atoms which is unsubstituted or substituted with a halogen atom; an oxygen atom; a sulfur atom; a selenium atom; or a group $—NR_{15}$, wherein $R_{15}$ is a hydrogen atom, a linear or branched alkyl group having 1 to 5 carbon atoms, or a linear or branched acyl group having 1 to 5 carbon atoms, and n is an integer of 0 to 6, or a salt thereof.

Examples of the linear or branched alkoxy group having 1 to 5 carbon atoms include a methoxy group, an ethoxy group, a propoxy group, an isopropoxy group, a butoxy group, an isobutoxy group, a sec-butoxy group, a tert-butoxy group and a pentyloxy group.

Examples of the linear or branched alkyl group having 1 to 5 carbon atoms include a methyl group, an ethyl group, a propyl group, an isopropyl group, a butyl group, an isobutyl group, a sec-butyl group, a tert-butyl group and a pentyl group.

Examples of the linear or branched acyl group having 1 to 5 carbon atoms include a formyl group, an acetyl group, a propionyl group, a butyryl group, an isobutyryl group, a valeryl group and an isovaleryl group.

Examples of the halogen atom include Cl, Br, I or F.

In a preferred embodiment, $R_1$ to $R_5$ are each independently a hydrogen atom; a halogen atom; a hydroxyl group; a linear or branched alkoxy group having 1 to 5 carbon atoms; or a linear or branched alkyl group having 1 to 5 carbon atoms which is unsubstituted or substituted with a halogen atom; wherein two adjacent groups among $R_1$ to $R_5$ may join together to form $—O—CH_2—O—$ or $—O—(CH_2)_2—O—$.

$R_2$ and $R_3$ are preferably a linear or a branched alkoxy group having 1 to 5 carbon atoms or join together to form —O—$CH_2$—O— or —O—$(CH_2)_2$—O—. Further preferably, $R_2$ and $R_3$ are a methoxy group, an ethoxy group or a propoxy group, and most preferably a methoxy group or an ethoxy group.

$R_1$, $R_4$ and $R_5$ are preferably a hydrogen atom.

In an embodiment, $R_6$ to $R_9$ are each independently a hydrogen atom; a halogen atom; a hydroxyl group; a linear or branched alkoxy group having 1 to 5 carbon atoms; a linear or branched alkyl group having 1 to 5 carbon atoms which is unsubstituted or substituted with a halogen atom; or a group —$NR_{12}R_{13}$, wherein $R_{12}$ and $R_{13}$ are each independently a hydrogen atom, an oxygen atom, or a linear or branched alkyl group having 1 to 5 carbon atoms which is unsubstituted or substituted with a halogen atom; wherein two adjacent groups among $R_6$ to $R_9$ may join together to form —O—$CH_2$—O— or —O—$(CH_2)_2$—O—, $R_6$ and $R_9$ are preferably each independently a hydrogen atom; a halogen atom; a hydroxyl group; a linear or branched alkoxy group having 1 to 5 carbon atoms; a linear or branched alkyl group having 1 to 5 carbon atoms which is unsubstituted or substituted with a halogen atom, more preferably a hydrogen atom.

In a preferred embodiment, $R_7$ by is a hydrogen atom; a halogen atom; a hydroxyl group; a linear or branched alkoxy group having 1 to 5 carbon atoms; a linear or branched alkoxy group having 1 to 5 carbon atoms which is substituted with a group —C(O)A, wherein A is a saturated or unsaturated 5- or 6-membered ring which is unsubstituted or substituted with a linear or branched alkyl group having 1 to 5 carbon atoms and the ring may contain 1 or 2 atoms independently selected from a nitrogen atom, an oxygen atom and a sulfur atom; a linear or branched alkyl group having 1 to 5 carbon atoms which is unsubstituted or substituted with a halogen atom; or a group —$NR_{12}R_{13}$, wherein $R_{12}$ and $R_{13}$ are each independently a hydrogen atom, an oxygen atom, or a linear or branched alkyl group having 1 to 5 carbon atoms which is unsubstituted or substituted with a halogen atom; $R_8$ is a hydrogen atom; a halogen atom; a hydroxyl group; a linear or branched alkoxy group having 1 to 5 carbon atoms; or a linear or branched alkyl group having 1 to 5 carbon atoms which is unsubstituted or substituted with a halogen atom; or $R_7$ and $R_8$ join together to form —O—$CH_2$—O— or —O—$(CH_2)_2$—O—.

In an embodiment, $R_7$ is a linear alkoxy group having 1 to 5 carbon atoms which is substituted with a group —C(O)A, and the group —C(O)A binds to the terminal carbon atom of the alkoxy group.

In a preferred embodiment, A contains at least one nitrogen atom, and examples of such A include a pyrrolidinyl, imidazolidinyl, pyrazolidinyl, pyrrolyl, imidazolyl, pyrazolyl, thiazolyl, isothiazolyl, oxazolyl, isooxazolyl, piperidinyl, piperazinyl, morpholinyl, pyridyl, pyrimidinyl, pyrazinyl and pyridazinyl groups which are unsubstituted or substituted with a linear or branched alkyl group having 1 to 5 carbon atoms. In a more preferred embodiment, A is a piperidinyl group, a piperazinyl group or a morpholinyl group which is unsubstituted or substituted with a linear or branched alkyl group having 1 to 5 carbon atoms. In a further preferred embodiment, A is a piperidin-1-yl group, a piperazin-1-yl group or a morpholin-4-yl group which is unsubstituted or substituted with a linear or branched alkyl group having 1 to 5 carbon atoms.

$R_{10}$ and $R_{12}$ are preferably a hydrogen atom.

In a preferred embodiment, X is an oxygen atom; a sulfur atom; or a group —$NR_{13}$, wherein $R_{15}$ is a hydrogen atom, a linear or branched alkyl group having 1 to 5 carbon atoms, a linear or branched acyl group having 1 to 5 carbon atoms. X is preferably a sulfur atom.

In a preferred embodiment, n is an integer of 0 to 4. In another preferred embodiment, n is 2 or 3.

In a preferred embodiment, the WNT signaling inhibitor is a compound selected from the following group:

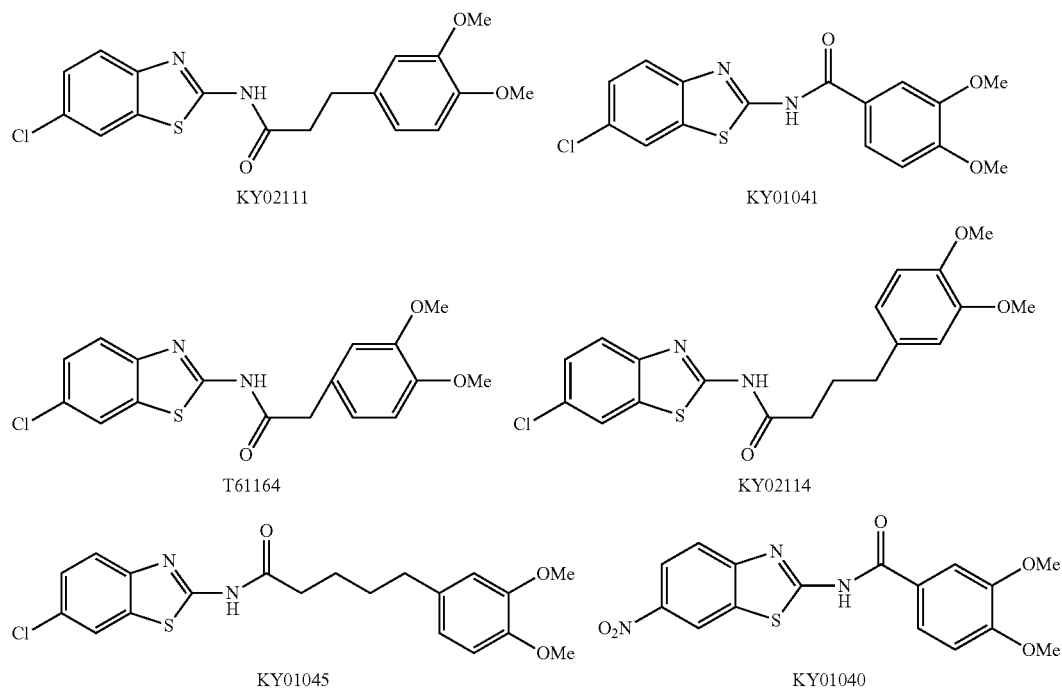

KY02111

KY01041

T61164

KY02114

KY01045

KY01040

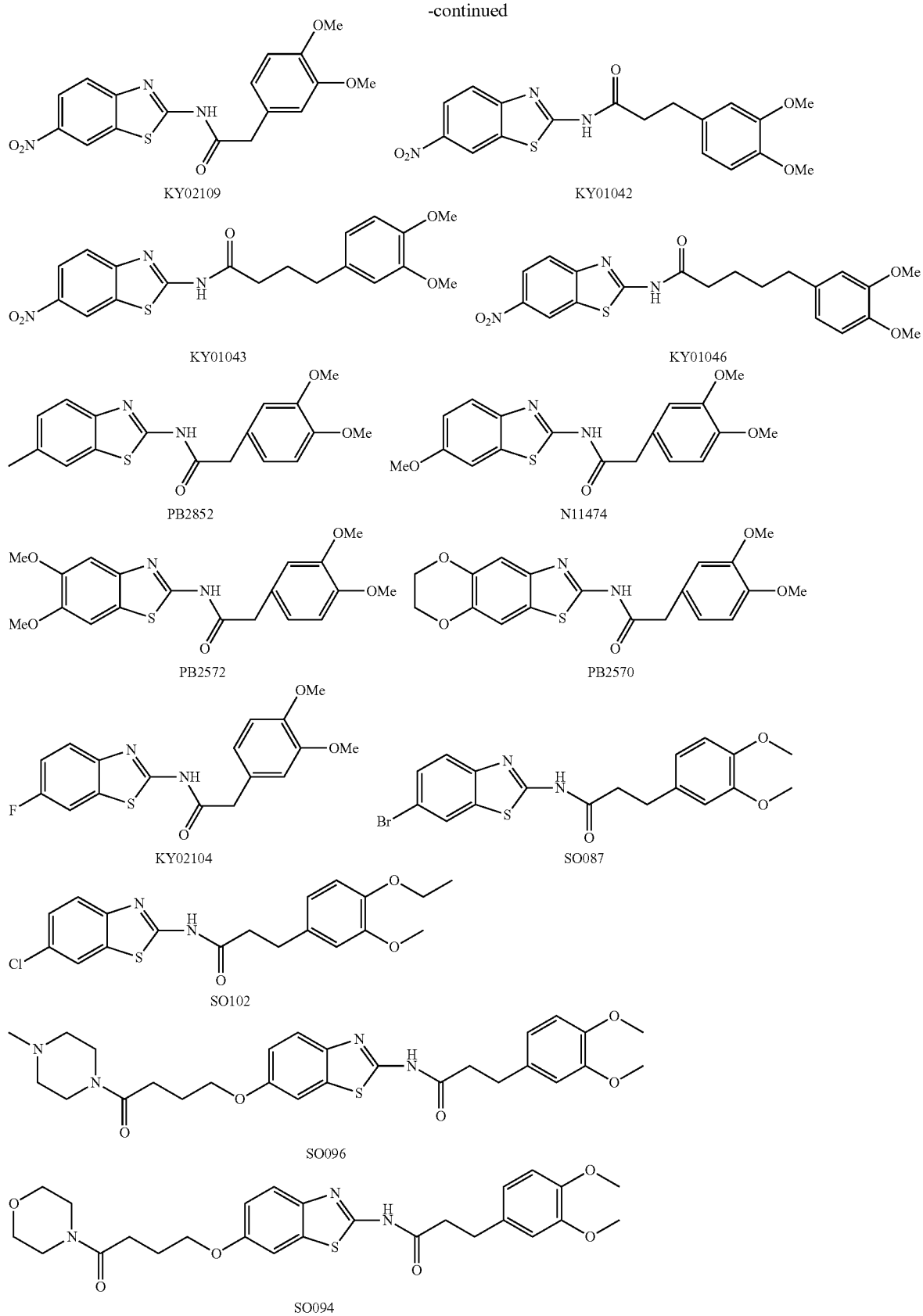
or a salt thereof.

The compound of Formula (I) can be synthesized by the known method (J. Med. Chem., 1965, 8 (5), pp 734-735) (incorporated herein by references) or in accordance with the method described in Examples.

Examples of the compound of Formula (I) are described in, for example, J. Med. Chem., 1965, 8 (5), pp 734-735 (incorporated herein by references) (N11474, T61164). Also, they are available from UkrOrgSynthesis Ltd. (PB2852, PB2572, and PB2570) and ENAMINE (T61164) and the like.

The medium used in the step (1), the step of culturing a pluripotent stem cell in a medium containing one or more WNT signaling activators, and the medium used in the step (2), the step of culturing a cell produced in the step (1) in a medium containing one or more WNT signaling inhibitor, may be any conventional medium used for cardiac differentiation of a pluripotent stem cell and the composition of the differentiation medium is not specifically limited. Examples of the medium include the IMDM-based medium for cardiac differentiation (for example, the medium used in the examples), DMEM-based medium for cardiac differentiation (200 ml DMEM/F12 medium (Sigma) containing 50 ml bovine fetal serum (GIBCO), 2.5 ml MEM non-essential amino acid solution (Sigma), 2.5 ml penicillin-streptomycin (GIBCO), 200 mM L-glutamine, and 2.5 ml 2-mercaptoethanol), and StemPro-34SFM (GIBCO)+BMP4 (10 ng/ml).

In the method of the invention, any conventional culture method suitable for cardiac differentiation of a pluripotent stem cell may be used. Examples of the culture method include adhesion culture, floating culture, and suspension culture. In the method of the invention, it is not necessary to use feeder cells such as END2 cells.

By the method of the invention, it is possible to efficiently induce cardiac differentiation of a pluripotent stem cell even when a medium which does not contain serum (i.e., "a serum-free medium") is used. When a serum-free medium is used, the medium preferably contains albumin and the cell is preferably cultured by adhesion culture. Examples of albumin include bovine serum albumin and human serum albumin. In the adhesion culture, the culture dish may be coated with gelatin or laminin (such as human laminin 211). When a serum free medium containing albumin is used in the method of the invention, it is possible to induce cardiac differentiation of a pluripotent stem cell in the absence of proteins other than albumin, such as serum, cytokines, and feeder cells, and components derived from species of organism different from the pluripotent stem cell used in the method (i.e., xenogeneic components).

In the method of the invention, the period from the start of culture in a medium for cardiac differentiation (i.e., culture for cardiac differentiation) to the start of the step (1) or (2) and the periods of the steps (1) and (2) of may be appropriately determined. The step (2) may be started just after the end of the step (1), or after a certain period from the end of the step (1). The WNT signaling activator and the WNT signaling inhibitor may be added at early and middle phases of cardiac differentiation of a pluripotent stem cell, respectively. The early phase of cardiac differentiation of a pluripotent stem cell means a stage at which differentiation of a pluripotent stem cell into mesoderm is induced and the expression of a mesoderm marker gene is increased. The middle phase of cardiac differentiation of a pluripotent stem cell means a stage at which differentiation of mesoderm into cardiac muscle is induced. Examples of the mesoderm marker includes T, MIXL1, and NODAL. For example, when a monkey or human ES or iPS cell is used, the step (1) may be conducted at Day 0 to Day 2 or Day 0 to Day 3 of culture for cardiac differentiation, in other words, for 2 or 3 Days from the start of culture for cardiac differentiation, and the step (2) may be conducted, up until Day 14 of culture for cardiac differentiation, for 2 days or more (specifically, for 2, 3, 4, 5, 6, 7, 8, 9, 10, 11, or 12 days), preferably for 3 to 10 days, more preferably for 4 to 10 days, still more preferably for 4 to 8 days, even more preferably for 4 to 6 days. Preferably, the step (2) is conducted for 4 to 6 days up until Day 10 of culture for cardiac differentiation, for example Day 3 to Day 9, Day 3 to Day 8, Day 3 to Day 7, Day 4 to Day 10, Day 4 to Day 9, or Day 4 to Day 8 of culture for cardiac differentiation.

Concentrations of the WNT signaling activator and WNT WNT signaling inhibitor are not particularly limited. When the WNT signaling activator is BIO or CHIR99021, the WNT signaling activator may be used at a final concentration of 100 nM to 100 µM, preferably 1 µM to 10 µM. When the WNT signaling inhibitor is the compound of Formula (I), or IWP2, XAV939, or IWR1, the WNT signaling inhibitor may be used, for example, at a final concentration of 0.5 to 20 µM, preferably 1 to 10 µM.

The method of the invention may be used to prepare a cardiomyocyte. Differentiation into a cardiomyocyte may be detected from the number of beating cardiac colonies, expression of a cardiac marker, expression of an ion channel, a response to an electrophysiological stimulus, or the like. Examples of the cardiac marker include α-MHC, β-MHC, cTnT, α-actinin, and NKX2.5. Examples of the ion channel include HCN4, Nav1.5, Cav1.2, Cav3.2 HERG1b and KCNQ1. The cardiomyocyte prepared by the method of the invention may be used for evaluation of drug safety in vitro or as a cardiomyocyte for transplant to treat heart diseases.

The present invention also provides a kit for promoting cardiac differentiation comprising one or more WNT signaling inhibitors and/or one or more WNT signaling activators which is used for the method of inducing cardiac differentiation of the invention.

The present invention is described further in detail with reference to the following examples.

EXAMPLES

1. Methods
(1) Culture of hESC, hiPSC, and Monkey ESC

All PSC lines were maintained on mitomycin C-treated mouse embryonic fibroblasts (MEF), in Primate ES Cell Culture Medium (ReproCELL Inc., Japan), with 5 ng ml$^{-1}$ bFGF for hPSCs, and without bFGF for monkey ESCs. Human ESC lines were KhES-1, KhES-3, H1, and H9 (Non-patent literatures 1, 41). Human iPSC lines were 253G1, IMR90-1, IMR90-4 (Non-patent literatures 42, 43), and RCHIPC0003. RCHIPC0003 was established from human fibroblasts by ReproCELL. The monkey ESC line was CMK6.4 (Non-patent literatures 1, 44, 45). The hESC line was used in conformity with the Guidelines for Derivation and Utilization of Human Embryonic Stem Cells of the Ministry of Education, Culture, Sports, Science, and Technology of Japan.

(2) Transgenic Monkey ESC Line

To generate human αMHC promoter-driven EGFP-expressing monkey ESCs, the 918 bp upstream from the transcriptional starting site and the third exon just before the open reading frame were amplified from genomic DNAs of KhES-1 hESCs by PCR, using the following primer sets —forward primer, 5'- CCAGGCACCTGCACCCTCTGG-3' (SEQ ID No: 37); reverse primer, 5'- (including a SalI linker)

22 TAGTCGACCTTGGTGCTTCCCCTGGGTCAGAG-3' (SEQ ID No: 38)—and then ligated into pGEM-T Easy Vector (Promega). The HindIII/SalI fragment from the cloning vector was connected with pEGFP-1 (Clontech). The linearized αMHC-EFGP vector was introduced into CMK6.4 monkey ESCs by electroporation. Transgenic ESC clones were selectively grown with G418 (Sigma-Aldrich). The expression of EGEP was confirmed in beating colonies.

(3) High Content Analysis (HCA) Screening of Small Molecules for Promotion of Cardiac Differentiation The confluent (4-5 d after passage) αMHC-GFP transgenic monkey ESCs were dissociated enzymatically by CTK solution (Non-patent literature 1), and the ESC clumps (40-100 µm in diameter) were obtained using 40 and 100 µm Cell Strainers (BD Biosciences). The ESC clumps (approximately $5.0 \times 10^3$ cells well$^{-1}$) were transferred onto 96-well plates (Greiner Bio-One, 96-well black plate, Cat. No. 655090) and incubated in cardiac differentiation medium as described in (4) below. During Days 6-14 of cardiac differentiation, 9600 compounds from the chemical library (dissolved in DMSO) were screened using 96-well plates. Sixteen and 80 wells were used for the control (0.1% DMSO) and chemical compounds (1 per well), respectively. Final concentration of the each compound was approximately 1-5 µM. Medium containing small molecules was changed every 4 d. On Day 14, GFP fluorescence of ESCs was measured by whole-plate scanning, using the Metamorph imaging system (Molecular Device). Metamorph software was used to analyze the GFP fluorescence data and calculate Fluorescence Area, Total Fluorescence Intensity, Average Fluorescence Intensity, and number of GFP-positive colonies for each well. Hit compounds were determined by the following criteria: Average Fluorescence Intensity of a well with the compound was >6 SD greater than Average Fluorescence Intensity of the control (mean of 16 wells), and Total Fluorescence Intensity for the compound was >0 SD greater than the control; or Total Fluorescence Intensity of the compound was >4 SD greater than the control, and Average Fluorescence Intensity of the compound was >0 SD greater than the control. One hundred and twenty compounds passed these criteria and were retested using 8 wells for each compound. Molecule N11474 significantly increased GFP fluorescence of ESCs compared to DMSO (Student's t-test, P=0.015).

(4) Cardiac Differentiation in Serum-containing Medium

Confluent hESCs and hiPSCs were gently detached with CTK solution and transferred into Petri dishes (BD Biosciences) with Primate ES Cell Culture Medium (ReproCELL, Japan). Cells were held in suspension culture for 8-24 h to form aggregates. The sizes of hPSC aggregates (0.3-1 mm in diameter) are important for efficient differentiation. Following suspension culture, cell aggregates were attached to culture dishes ($3-10 \times 10^5$ cells cm$^{-2}$) in cardiac differentiation medium: IMDM (Sigma), containing 20% FBS (Gibco), 1% MEM non-essential amino acid solution (Sigma), 1% Penicillin-Streptomycin (Gibco), 2 mM L-glutamine (Sigma), 0.001% 2-Mercaptoethanol (Gibco), and 0.005N NaOH, with 10 ng ml$^{-1}$ BMP4 (R&D Systems). The medium was changed to cardiac differentiation medium with 10 µM KY02111 and/or other WNT inhibitors added on Day 3 (hiPSC lines) or Day 4 (human or monkey ESC lines); XAV939 (Wako, Japan), IWP-2 (Santa Cruz Biotechnology), IWR-1 (Merck4Bioscience), IGFBP4 (R&D Systems), Dkk1 (R&D Systems) and the mixture of bFGF (R&D Systems), BMP4 (R&D Systems), VEGF (R&D Systems), DKK1 (R&D Systems), and Activin A (R&D Systems) (Non-patent literature 16). Medium was changed every 2-3 d. KY02111 and other WNT inhibitors were added until Day 9 for hiPSC lines and the monkey ESC line, or Day 14 for hESC lines. On Day 15, cardiac cell colonies on dishes were incubated with protease solution (0.1% collagenase type I, 0.25% trypsin, 1 U ml$^{-1}$ DNase I, 116 mM NaCl, 20 mM HEPES, 12.5 mM NaH2PO4, 5.6 mM glucose, 5.4 mM KCl, and 0.8 mM MgSO4, pH 7.35) for 0.5-2 h, until all cardiac colonies were detached from the bottom of the wells. The detached cardiac colonies were transferred into 15 ml tubes with fresh cardiac differentiation medium and precipitated by gravity, and the supernatant was removed by aspiration. The cardiac colonies were then transferred into Ultra-low culture dishes (Corning, 3261) or 6-well plates (Corning, YO-01835-24) in cardiac differentiation medium without both serum and NaOH. The floating cardiac colonies were maintained for more than 1 month, and the media were changed every 5 d. A differentiation method of mouse ESC (R1 line) was carried out as previously described[46], and KY02111 was added during Days 3-6. Beating colonies were counted on Day 9.

(5) Cardiac Differentiation in Serum-Free and Defined Medium

After pre-culture in Petri dishes as described above, cell aggregates were attached to culture dishes coated with gelatin (Sigma G2625) or human laminin 211 (BioLamina, Sweden) at $3-10 \times 10^5$ cells cm$^{-2}$, in serum-free cardiac differentiation medium: IMDM (Sigma) containing 1% MEM non-essential amino acid solution (Sigma), 1% Penicillin-Streptomycin (Gibco), 2 mM L-glutamine (Sigma), 0.5 mM L-carnitine (Sigma), 0.001% 2-Mercapcoethanol (Gibco), and 1-2% bovine serum albumin (Wako, Japan) or 0.4% human serum albumin (Sigma), with 5 µM CHIR99021 (Axon) and 2 µM BIO (Calbiochem). On Days 3-9, 10 µM KY02111 and/or other WNT inhibitors (XAV939 and/or IWP-2) were added to cell cultures, and the medium was changed every 2 d. On Day 15, the cardiac colonies were incubated with the protease solution for 5-10 min, until all colonies were detached from the bottom of the wells. The cardiac colonies were transferred into 15 ml tubes with cardiac differentiation medium including 0.1% albumin, and precipitated by gravity, the supernatant was removed, and the cardiac colonies were transferred to Ultra-low culture 6-well plates (Corning, YO-01835-24) with cardiac differentiation medium including 0.1% albumin. The floating cardiac colonies were maintained for more than 1 month, and the media were changed every 5 d.

(6) Immunostaining and Flow Cytometry

Cardiac colonies were dissociated by stirring for 1-2 h at 37° C. with the protease solution described above, cultured for 1 d on cover glasses coated with gelatin (Sigma), and fixed with 4% paraformaldehyde. After permeabilizing with Triton X, the cells were treated with 2% skim milk for 1-2 h, then incubated with primary antibodies for 2 h: NKX2.5 (rabbit polyclonal, 1:250; Abcam), αActinin (mouse monoclonal, 1:800; Sigma), cardiac TnT (mouse monoclonal, 1:100; Santa Cruz Biotechnology), Vimentin (mouse monoclonal, 1:800; Sigma V6630), and HCN4 (mouse monoclonal, 1:400; Abcam). The secondary antibodies used were Alexa546-conjugated anti-mouse IgG, Alexa488-conjugated anti-mouse IgG, and Alexa488-conjugated anti-rabbit IgG (1:1000; all from Molecular Probes, Invitrogen). Nuclei were visualized by DAPI. Images were captured under fluorescent microscopy (Olympus). The number of cTnT, αActinin, NKX2.5, HCN4, and Vimentin-positive cells were counted from three random areas, using the Metamorph imaging system (Molecular Devices). Approximately 1000 DAPI-stained cells were used to calculate the proportion of immunopositive cells (the number of immunopositive cells divided by the number of DAPI-stained cells). For flow cytometry, single cells from hPSC-derived cardiac colonies were stained by anti-cTnT antibody and Alexa488-conjugated anti-mouse IgG second antibody. Cells were analyzed using a FACS CantoII flow cytometer (BD Biosciences). Data was analyzed using FACADiva software (BD Biosciences).

(7) Microarray Experiments

IMR90-1 iPSCs were cultured in cardiac differentiation medium containing serum. On Day 3, cells were treated with 10 μM KY02111 or 0.1% DMSO for 0, 12, or 24 h. Non-treated cells (0 h), cells treated with KY02111 for 12 h (KY12hr) or 24 h (KY24hr), and cells treated with 0.1% DMSO for 12 h (DMSO12hr) or 24 h (DMSO24hr) were used for microarray analysis. Total RNA was prepared using the RNeasy Mini Kit (Qiagen), according to the manufacturer's instructions. Synthesis of cDNA, in vitro transcription and biotin labeling cRNA, and hybridization to the Human Gene 1.0 ST array (Affymetrix) were performed according to Affymetrix protocols. Hybridized arrays were scanned using an Affymetrix GeneChip Scanner. Data normalization and further analysis were performed with GeneSpring GX (Agilent Technologies). Proportions of treated cells expressing genes relative to control (KY02111/DMSO) were calculated for each time point. Genes that were down-regulated or up-regulated in response to KY02111 were identified as have >25% change in KY/DMSO ratio at both 12 and 24 h after KY02111 treatment (down-regulated genes=KY12h/DMSO12h<0.75 and KY24h/DMSO24h<0.75; up-regulated genes=KY12h/DMSO12h>1.25 and KY24h/DMSO24h>1.25). The microarray data have been submitted to the Gene Expression Omnibus (GEO) public database at NCBI (GEO accession number, GSE33622). For analysis of Distant Regulating Elements of co-regulated genes (DiRE analysis), all or the top ten down-regulated genes (based on the KY12h/DMSO12h ratio) were analyzed using the web-based program (http://dire.dcode.org/) (Non-patent literature 35).

(8) qRT-PCR

Total RNA was isolated with an RNeasy Mini Kit (QIAGEN). Genomic DNA was completely digested with DNase I (Invitrogen). Total RNA (0.5 μg) was subjected to cDNA synthesis using the SuperScript III Reverse Transcriptase (Invitrogen). qRT-PCR was performed in triplicate, using SYBER GREEN PCR Master Mix on a 7500 Real Time PCR System (Applied Biosystems). The cycling conditions were as follows: 10 min at 95° C.; 40 cycles, each consisting of 15 s at 95° C.; 1 min at 60° C. Total RNA from human adult heart tissue (BioChain) was used to evaluate the expression levels of cardiac marker genes for cardiomyocytes derived from hPSCs. All values were normalized with respect to GAPDH expression level and expressed relative to the corresponding values in human adult hearts (100%). All of the primer sets are listed in Table 1.

(9) TOPFlash Assay

For the TCF reporter assay, IMR90-1 hiPSCs were cultured in the serum-containing differentiation culture, as described above, and transfected with TOPFlash plasmid (Millipore 21-170) and pRL-SV40 plasmid (Renilla luciferase transfection control, Promega E1980) on Day 2, using FuGENE HD transfection Reagenet (Promega E2311). After 24 h, 10 μM KY02111, 10 μM XAV939, or 10 μM IWP-2 was added to the medium, along with either 60 ng ml$^{-1}$ of mouse Wnt3a (Wako 232-02421) or 3 μM BIO. After 48 h of transfection (Day 4), luciferase activities were measured using a Dual-Luciferase Reporter 1000 Assay System kit (Promega E1980) and a 2030 ARVO X3 plate reader (PerkinElmer). Luciferase activities were normalized to the luminescence of the transfection control, Rennila luciferase, according to the kit protocol. For experiments using HEK293 cells, the cells were cultured in 10% FBS DMEM medium, and transfected with TOPflash and pRL-SV40 plasmid, using FuGENE HD. After 24 h, the transfected cells were seeded onto 96-well plates (10,000 cells well$^{-1}$) in medium containing 10 μM KY02111, 10 μM XAV939, or 10 μM IWP-2, along with 3 μM BIO or 60 ng ml$^{-1}$ mouse Wnt3a. Luciferase activities were measured 48 h after transfection by the procedure described above.

(10) Patch-Clamp Recordings

Cells were isolated from beating hPSC-derived cardiomyocytes, using protease solution. The dissociated cells were cultured for 3-7 d on gelatin-coated cover glasses. Patch-clamp recordings were performed in a temperature-controlled room at approximately 25° C. Data from the whole cell patch-clamp configuration were recorded from spontaneously beating cells, using a HEKA EPC10 amplifier (HEKA Instruments Inc.). An external solution containing 140 mM NaCl, 5 mM KCl, 10 mM HEPES, 2 mM $CaCl_2$, 1 mM $MgCl_2$, and 10 mM glucose was adjusted to pH 7.2 with NaOH. A pipette solution containing 80 mM K-aspartate, 50 mM KCl, 1 mM $MgCl_2$, 10 mM EGTA, 3 mM ATP-Mg, and 10 mM HEPES was adjusted to pH 7.2 with KOH. In some experiments, cells were treated with 0.1 μM E4031, 4 μM chromanol 293B, 4 μM zatebradine, 1 μM tetradotoxin (TTX), or 4 μM nifedipine for 5 min. The inhibitors were obtained from Sigma-Aldrich. One mM stock solutions of E4031 and TTX were prepared with $H_2O$. Twenty millimolar stock solutions of chromanol 293B, zatebradine hydrochloride, and nifedipine were prepared with DMSO. All stock solutions were stored at −20° C. until use. The current-voltage relationship was obtained by holding the membrane potential at −40 to −60 mV, and delivering a depolarizing pulse for 500 ms in a stepwise manner, in increments from −60 to 60 mV for INa, −40 to 40 mV for ICaL, −40 to 40 mV for IKs and IKr, and −50 to −140 mV for Ih.

(11) QT Interval Prolongation Assay

Microelectrode array (MEA) dishes (Multi Channel Systems, Reutlingen, Germany) were coated with ReproCoat (RCESD006, ReproCELL, Japan) in 5% $CO_2$ for 1 h at 37° C. After coating, KY02111-induced cardiomyocytes at Day 30 were transferred into 1 ml of Cardiomyocyte Culture Medium (RCESD006, ReproCELL, Japan) on the MAE dish. Using a pipet tip or glass bar, the cardiomyocytes were gently moved onto the electrode and cultured overnight to attach to the MEA dishes. On the following day, the medium was changed into Cardiomyocyte Test Medium (RCESD003, ReproCELL, Japan). After confirming the presence of beating cardiomyocytes, the MEA dishes were attached to an MEA amplifier (Multi Channel Systems, Reutlingen, Germany), and electrocardiogram-like waves were recorded. After 2 min of recording, 300 pM astemizole (Sigma) or 0.1% DMSO were added, and the concentrations of astemizole (300 pM to 30 μM) were increased every 4 min. ECG-like waves were recorded after 2 min of each astemizole treatment. Beating rate, $Na^+$ amplitude, $K^+$ amplitude, and $Na^+$—$K^+$ interval were analyzed by LabChart™ software v7 (ADInstruments, Adelaide, Australia).

(12) Statistical Analysis

All results were expressed as mean±SEM. Unpaired two-tailed student t-tests were used to compare mean values of measurements from different treatments. Differences were considered significant at $P<0.05$.

(13) Chemical Synthesis

KY02111, KY01041, KY02114, KY01045, KY01040, KY02109, KY01042, KY01043, KY01046, and KY02104 were prepared as described in "3. Preparation Examples" below. PB2852, PB2572, and PB2570: PB285238764, PB257239592 and PB257074412 were purchased from UkrOrgSynthesis. T61164: T6116478 was purchased from ENAMINE.

2. Results (1) Discovery and Characterization of KY02111

To identify small molecules that efficiently promote cardiomyocyte differentiation from hPSCs, we established a high-content analysis (HCA) system, using monkey ES cells (ESCs) that, express EGFP driven by human αMHC promoter (FIG. 1a). The chemical screening for an enhanced GFP signal is described in "1. Methods". We identified one molecule, N11474, that significantly enhanced the values of HCA parameters, including GFP intensity and fluorescence area, compared to the control (Student's t-test, P=0.015).

During chemical screening, monkey ESCs were treated with small molecules for eight days (Days 6-14). To determine the period during which N11474 effectively promotes differentiation, we used several treatment patterns and observed the total signal intensity of αMHC promoter-driven EGFP on Day 14 (FIG. 1b). N11474 treatment on Days 6-10 was similarly effective to the screening protocol, and treatment after Day 8 (Days 8-12 or Days 10-14) was less effective. Treatment on Days 4-8 maximized the increase in GFP expression, while treatment on Days 0-4 completely repressed GFP expression. These results suggested that N11474 acts as an inhibitor in the early phase (Days 0-4) of cardiac differentiation in monkey ESCs, and as a promoter in the middle phase (Days 4-8).

We chemically synthesized analogs of N11474 and assayed their ability to promote cardiac differentiation of monkey ESCs. Structure-activity relationship studies revealed that substitution of the methoxy group at the benzothiazole ring with an electron-withdrawing group, and adjustment of the length of the methylene linker, greatly improved biological activity, resulting in a new molecule, KY02111 (FIG. 1c,d; FIG. 5a-c). This drug-like small molecule promoted cardiac differentiation about 73 times more effectively than the DMSO control, and 7.4 times more effectively than N11474 (FIG. 1d).

The general applicability of KY02111's activity was examined with a variety of primate and rodent PSCs. KY02111 increased the ratio of beating cardiac colonies as much as 60-94% in cell aggregates of two human ESC lines (KhES-1 and KhES-3), four human iPSC lines (253G1, IMR90-1, IMR90-4, and RCHIPC0003), and a mouse ESC line (R1) (FIG. 1e). Time-course experiments using hiPSCs (IMR90-1) showed that beating colonies emerged on Day 10 and increased in number until Day 25 (FIG. 6). When beating colonies were subcultured, the subsequent proportion of beating colonies increased up to 90% (FIG. 6), probably due to reduced mechanical inhibition (Non-patent literature 33). The cardiac colonies continued beating until at least Day 50 (FIG. 6).

(2) Characterization of Cardiomyocytes Produced by KY02111

Immunocytochemistry showed that approximately 73-85% of hiPSCs (IMR90-1) treated with KY02111 expressed the cardiac markers, cardiac troponin T (cTnT), α-actinin, or NKX2.5, while only a few DMSO-treated cells were positive for the markers (FIG. 2a,b). The cardiac pacemaker marker, HCN4, was expressed in 16% of KY02111-treated cells, while the ratio of Vimentin-positive cells (fibroblasts) decreased 3.3-fold (FIG. 2b). SMA, a marker of smooth muscle, was almost undetectable in KY02111-treated cells (data not shown). Those results indicate that it is possible to enrich hPSC-derived cardiomyocytes by collecting colonies of KY02111-induced cells without the process of cell sorting. Real-time PCR analysis on Days 15 and 30 showed that KY02111-induced cardiomyocytes (KY-CMs) expressed the cardiac markers, αMHC, NKH2.5, and HCN4, and that all of the ion channel genes examined were expressed at levels equivalent to those of adult heart tissue (FIG. 2c).

Electrophysiological analysis by the whole-cell patch-clamp method was used to examine whether KY-CMs are functional cells. Action potential properties indicated that the population of KY-CM included ventricular cells and pacemaker cells (FIG. 2d). The properties of voltage-dependent $Ca^{2+}$, $Na^+$, and HCN channel currents were examined using the ion channel blockers, Nifedipine, Lidocaine, and Zatebrazine, respectively (FIG. 7a-c). The current density-voltage relationships indicated that KY-CMs were electrophysiologically functional. Treatment of KY-CMs with HERG channel blocker, E4031, and KCNQ1 channel blocker, Chromanol293B, increased action potential duration (APD), which is equivalent to QT prolongation detected by an electrocardiogram (ECG) (FIG. 2e). The increases in duration of APD90 (APD at 90% repolarization) were 37.0%±11.2 for E4031 treatment, and 42.1%±8.8 for Chromanol293B treatment (FIG. 2e and FIG. 7e). Moreover, voltage-dependent $K^+$ currents were suppressed by treatment with E4031 and Chromanol293B (FIG. 7d,e). These results indicated that the KY-CMs expressed functional HERG and KCNQ1 channels. A drug-induced QT prolongation test, performed using a microelectrode array, showed that ECG-like waves were emitted from KY-CM colonies (FIG. 8a,b). Treatment with Astemizole, which causes clinical QT prolongation (Non-patent literature 34), prolonged the $Na^+$—$K^+$ interval of the ECG-like waves in a dose-dependent manner (Supplementary FIG. 4c). Overall, these results indicated that KY-CMs are electrically and pharmacologically functional.

(3) Inhibition of Canonical WNT Signaling Pathway by KY02111

To gain insight into how KY02111 promotes cardiac differentiation of hPSCs, gene expression profiles of hiPSCs (IMR90-1) treated with KY02111 were analyzed using the microarray technique. KY02111 or DMSO was added to the culture on Day 3 of cardiac differentiation (the optimal starting point for IMR90-1 cells), and the cell population was harvested after 12 or 24 h. Twenty-two down-regulated genes and four up-regulated genes were identified at both 12 h and 24 h after KY02111 treatment (FIG. 3a and Table 2). Although only a few genes were extracted by the microarray analysis, perhaps due to high heterogeneity of the cell population, the microarray data were validated by qPCR (FIG. 9a). When the 22 down-regulated genes were examined for common transcription factor-binding sites, using DiRE (Non-patent literature 35), which can predict distant regulatory elements, TCF4 was predicted as a common transcription factor (FIG. 9b). When the top 10 genes that were most down-regulated in the treated cells were examined, both LEF1 and TCF4 were predicted as common transcription factors (FIG. 9c). Sixteen of the 22 down-regulated genes (70%) were known target genes of canonical WNT signaling (Table 2). Furthermore, the effect of KY02111 on WNT target genes was very similar to the effect of other WNT inhibitors, such as XAV939 and IWP-2, but not to the effect of BIO, a WNT activator (FIG. 9d). These results suggested that KY02111 inhibits canonical WNT signaling in hPSCs.

The TOPflash assay, a reporter system generally used for measuring activities of canonical WNT signaling, was used to confirm that KY02111 is a novel WNT signaling inhibitor. IMR90-1 cells were transfected with TOPflash and pRL- SV40, then were treated with Wnt3a or BIO, along with KY02111 or other WNT inhibitors. Treatment with KY02111 or XAV939, a known WNT inhibitor, clearly reduced luciferase activities (FIG. 9e). TOPflash results using Wnt3a or BIO suggested that KY02111 is an inhibitor of canonical WNT signaling. Interestingly, the TOPflash assay using HEK293 cells in the presence of Wnt3a showed that KY02111 enhanced luciferase activity, but the assay using BIO instead of Wnt3a showed that KY02111 cancelled WNT activation by BIO (FIG. 9f). Although this activity might depend on the cell line, KY02111 does have an inhibitory effect on WNT signaling in hPSCs.

(4) Synergistic Effect of WNT Inhibitors and KY02111

Next, promotion of cardiac differentiation was compared in transgenic monkey ESCs between KY02111, several chemical or proteinaceous WNT inhibitors (IWP-2, IWR-1, XAV939, DKK1, and IGFBP4 (Non-patent literature 36)), and a combination of several cytokines. As expected, all of them increased the intensity of the GFP signal driven by αMHC promoter, but KY02111 was most effective, and the other chemical WNT inhibitors were more effective than the proteinaceous factors or cytokines (FIG. 3b, c). Treatment with KY02111 increased differentiation about 80-fold compared to the control. Treatment with KY02111 was also most effective in promoting cardiac differentiation of hiPSCs (FIG. 3d). Although the total number of differentiated cells generated was similar among the inhibitors (FIG. 10a), the proportions of beating colonies were different: 87, 37, and 7.5%, for KY02111, IWP-2, and XAV939, respectively (FIG. 3d). The proportions of cTnT-positive cells showed similar trends to the proportions of beating colonies (FIG. 10b).

When BIO was added along with IWP-2 or XAV939, cardiac differentiation of monkey ESCs and hiPSCs was completely inhibited, while cardiac differentiation promoted by KY02111 was not affected by BIO (FIG. 3c,d). These results suggest that the mechanism of WNT inhibition by KY02111 is different from that of IWP-2 or XAV939, which inhibit O-acyltransferase PORCN or poly ADP-ribose polymerase TNKS, respectively (Non-patent literatures 22, 31). It appears that KY02111 might act downstream from GSK3β in the canonical WNT signaling pathway.

Because targets differ among WNT inhibitors, we examined whether the use of combined WNT inhibitors might increase differentiation of pluripotent stem cells to cardiomyocytes. KY02111 alone produced approximately 80% cTnT-positive cells from IMR90-1 iPSCs; KY02111 in combination with other WNT inhibitors did not significantly increase differentiation efficiency (FIG. 10b). However, treatment with combined WNT inhibitors did significantly enhance total cell numbers and beating colony numbers compared to treatment with KY02111 alone (FIG. 3e, FIG. 10a). The number of cardiomyocytes produced was 80-fold higher in the KY02111 and 130- to 220-fold higher in the combined treatments (KY+XAV, KY+IWP, and KY+XAV+IWP) than in the control (FIG. 3e).

(5) Defined, Cytokine-free and Xeno-free Cardiac Differentiation

When differentiation efficiency in serum-free medium was examined, two requirements were found: surface coating with gelatin or human laminin211, and addition of 0.4% human serum albumin or 1-2% bovine serum albumin. Non-attached cells were minimally differentiated into cardiomyocytes, and cell death occurred in serum-free medium without albumin (data not shown).

Activation of WNT signaling is required for the early phase of cardiac differentiation in hPSCs. Therefore, the effect of WNT activators, BIO and CHIR99021, was examined in the early stage of differentiation, in the absence of the cytokine, BMP4 (FIG. 4a). Treatment with BIO and CHIR99021 on Days 0-3, following treatment with KY02111 alone or with KY02111 and XAV939 (KY+XAV), resulted in 84-98% differentiation of IMR90-1 hiPSCs in both serum-containing medium and serum-free, albumin-containing medium (FIG. 4b,c). These results suggest that exogenous BMP4 and serum are not essential, and that small molecule-mediated activation of WNT signaling and endogenous signaling factors are sufficient to induce cardiac differentiation.

Treatment with KY+XAV did not result in significantly different differentiation efficiency than treatment with KY02111 (FIG. 4b). However, FACS analysis showed that, under cytokine- and serum-free conditions, treatment with KY+XAV had slightly higher efficiency (98.1%) than treatment with KY02111 alone (90.2%) (FIG. 4d). Immunostaining analysis showed, furthermore, that treatment with KY+XAV produced a higher proportion of cTnT-positive cells (97.7%±0.8) than KY02111 alone (93.3%±4.4) (FIG. 4b,c). Thus, the combined use of KY+XAV appears to result in highly efficient cardiac differentiation of hPSCs.

Treatment with KY02111 and serum gave a lower differentiation efficiency (83.7%±8.0) than treatment with KY02111 and albumin (93.3%±4.4) (FIG. 4b). The numbers of beating colonies and cardiomyocytes were about three times higher in serum-free KY02111 treatment than in KY02111 treatment with serum (FIG. 4e). Similarly, treatment with KY+XAV without serum enhanced the numbers of beating colonies and cardiomyocytes approximately 1.5-fold over treatment with serum (FIG. 4e). These results suggest that FBS might contain factor(s) that inhibit cardiac induction and/or proliferation of cardiac progenitors.

Additional experiments confirmed that other hPSCs (KhES-3, H1, H9, and 253G1) efficiently differentiated into cardiomyocytes in cytokine- and xeno-free, defined medium with KY02111, BIO, CHIR99021, and XAV939. As observed in IMR90-1 hiPSCs, these treatments enhanced the proportions of beating colonies and cTnT-positive cells in all cell lines tested (FIG. 11a,b). Immunostaining of cTnT and α-Actinin, furthermore, clearly showed sarcomere structures in cardiomyocytes derived from IMR90-1 hiPSCs (FIG. 11c). Overall, these results showed that the KY02111 differentiation method, using WNT signal-modulating small molecules and defined medium, effectively produced a high proportion of functional cardiomyocytes from hPSCs.

TABLE 1

Primer list for qPCR experiments

| Gene name | Forward | Reverse |
|---|---|---|
| HOXA1 | ACCCCTCGGACCATAGGATTAC (SEQ ID NO: 1) | AAGGCGCACTGAAGTTCTGTG (SEQ ID NO: 2) |
| MSGN1 | Origene HP204818 | |

TABLE 1-continued

Primer list for qPCR experiments

| Gene name | Forward | Reverse |
|---|---|---|
| T | CAACCTCACTGACGGTGAAAAA (SEQ ID NO: 3) | ACAAATTCTGGTGTGCCAAAGTT (SEQ ID NO: 4) |
| DKK1 | CCTTGGATGGGTATTCCAGA (SEQ ID NO: 5) | CCTGAGGCACAGTCTGATGA (SEQ ID NO: 6) |
| NODAL | TGTTGGGGAGGAGTTTCATC (SEQ ID NO: 7) | GCACAACAAGTGGAAGGGAC (SEQ ID NO: 8) |
| FGF4 | CCAACAACTACAACGCCTACGA (SEQ ID NO: 9) | CCCTTCTTGGTCTTCCCATTCT (SEQ ID NO: 10) |
| AXIN2 | CCCAAGCCCCATAGTGCCCAAAG (SEQ ID NO: 11) | CAGGGGAGGCATCGCAGGGTC (SEQ ID NO: 12) |
| MIXL1 | GGTACCCCGACATCCACTT (SEQ ID NO: 13) | TGGAAGGATTTCCCACTCTG (SEQ ID NO: 14) |
| αMHC | CTCAAGCTCATGGCCACTCT (SEQ ID NO: 15) | GCCTCCTTTGCTTTTACCACT (SEQ ID NO: 16) |
| βMHC | ACAAGCTGCAGCTAAAGGTC (SEQ ID NO: 17) | TCAAGATGTGGCAAAGCTAC (SEQ ID NO: 18) |
| NKX2.5 | ACCCTGAGTCCCCTGGATTT (SEQ ID NO: 19) | TCACTCATTGCACGCTGCAT (SEQ ID NO: 20) |
| αActinin | CTGCTGCTTTGGTGTCAGAG (SEQ ID NO: 21) | TTCCTATGGGGTCATCCTTG (SEQ ID NO: 22) |
| HCN4 | GGTGTCCATCAACAACATGG (SEQ ID NO: 23) | GCCTTGAAGAGCGCGTAG (SEQ ID NO: 24) |
| Nav1.5 | GAGCAACTTGTCGGTGCTG (SEQ ID NO: 25) | GATTTGGCCAGCTTGAAGAC (SEQ ID NO: 26) |
| Cav1.2 | CATGCTCACGGTGTTCCA (SEQ ID NO: 27) | CATGCTCACGGTGTTCCA (SEQ ID NO: 28) |
| Cav3.2 | CTATGCTGCGCTGGGAGT (SEQ ID NO: 29) | CTCGCAGGGGTTGTCTTC (SEQ ID NO: 30) |
| HERG1B | ACGCTTACTGCCAGGGTGAC (SEQ ID NO: 31) | GCCGACTGGCAACCAGAG (SEQ ID NO: 32) |
| KCNQ1 | CCACCTCAACCTCATGGTG (SEQ ID NO: 33) | ACAGTGAGGGCTTCCCAAT (SEQ ID NO: 34) |
| GAPDH | ATGGAAATCCCATCACCATCTT (SEQ ID NO: 35) | CGCCCCACTTGATTTTGG (SEQ ID NO: 36) |

TABLE 2

Significantly changed genes after KY02111 treatment (1)

| Down-regulated gene | Description | Wnt signaling |
|---|---|---|
| HOXA1 | homeobox A1 | Wnt downstream (Dev Dyn. 2010 January; 239(1): 126-39) |
| MSGN1 | mesogenin 1 | Wnt downstream (Nat Commun. 2011 Jul. 12; 2: 390) |
| NKD1 | naked cuticle homolog 1 | Wnt downstream Wnt inhibition (PLoS One. 2009 Nov. 24; 4(11): e7982) |
| T | brachyury | Wnt downstream (Mech Dev. 2000 Mar. 1; 91(1-2): 249-58) |
| TNFRSF11B | tumor necrosis factor receptor superfamily, member 11b | Wnt downstream (Bone. 2005 April; 36(4): 585-98) |
| DKK1 | dickkopf homolog 1 | Wnt downstream, Wnt inhibition (Oncogene. 2004 Nov. 4; 23(52): 8520-6) |
| DKK4 | dickkopf homolog 4 | Wnt downstream, Wnt inhibition (Dev Biol. 2007 May 15; 305(2): 498-507) |
| CDX2 | caudal type homeobox 2 | Wnt inhibition (Carcinogenesis. 2010 February; 31(2): 159-66) |
| MSX1 | msh homeobox 1 | Wnt downstream (Dev Biol. 2007 Nov. 15; 311(2): 665-78) |
| NODAL | nodal homolog | Wnt downstream (Neuron. 2007 Aug. 2; 55(3): 393-405) |
| FGF4 | fibroblast growth factor 4 | Wnt downstream (Genes Dev. 2002 Dec. 15; 16(24): 3173-85) |

TABLE 2-continued

| | | |
|---|---|---|
| PAPPA | pregnancy-associated plasma protein A, pappalysin 1 | Degradation of IGFBP4 (FEBS Lett. 2001 Aug. 24; 504(1-2): 36-40) |
| PRRX1 | paired related homeobox 1 | |
| LRAT | lecithin retinol acyltransferase | |
| CYP1B1 | cytochrome P450, family 1, subfamily B, polypeptide 1 | |
| SLC34A2 | cytochrome P450, family 1, subfamily B, polypeptide 1 | |
| AXIN2 | axin 2 (conductin, axil) | Wnt downstream (Mol Cell Biol. 2002 February; 22(4): 1172-83) |
| LGI1 | leucine-rich, glioma inactivated 1 | |
| SP5 | Sp5 transcription factor | Wnt downstream (Curr Biol. 2005 Mar. 29; 15(6): 489-500) |
| MIXL1 | Mix1 homeobox-like 1 | Wnt downstream (PLoS One. 2010 May 19; 5(5): e10706) |
| APCDD1 | adenomatosis polyposis coli down-regulated 1 | Wnt inhibition (Nature. 2010 Apr. 15; 464(7291): 1043-7) |
| | | Wnt downstream (Genes Chromosomes Cancer. 2006 June; 45(6): 565-74) |
| DSEL | dermatan sulfate epimerase-like | |

| Significantly changed genes after KY02111 treatment (2) | |
|---|---|
| Up-regulated gene | |
| FAM27D | family with sequence similarity 27, member D1 |
| CCT8L2 | chaperonin containing TCP1, subunit 8 (theta)-like 2 |
| | Transcripts Cluster Id: 8052087 |
| | Transcripts Cluster Id: 7908328 |

3. Preparation Examples

KY01041

3,4-Dimethoxybenzoylyl chloride (100 mg, 0.55 mmol) and triethylamine (83.0 μl, 6 mmol) were dissolved in methylene chloride (500 μl), 2-amino-6-chlorobenzothiazole (105 mg, 0.57 mmol) was added thereto, and the mixture was stirred for 1 hour at room temperature. After completion of the reaction, the reaction solution was diluted in methylene chloride and washed with a saturated saline solution. The solution was dried over magnesium sulfate and the solvent was evaporated. Ethanol was added to the residue, which was heated to 70° C., dissolved and recrystallized by cooling the temperature to room temperature, thereby obtaining 130 mg of 2-(3,4-dimethoxybenzamide)-6-chlorobenzothiazole in a yield of 68%.

$^1$H NMR (CDCl$_3$): δ10.15 (s, 1H), 7.83 (d, J=1.8 Hz, 1H), 7.63-7.45 (m, 3H), 7.36 (dd, J=1.8, 8.7 Hz, 1H), 6.91 (d, J=8.2 Hz, 1H), 3.96 (s, 3H), 3.94 (s, 3H)

MS (ESI) Found: 349 [M+H]$^+$

KY02111

Using 3-(3,4-dimethoxyphenyl)propanoyl chloride (100 mg, 0.42 mmol) and 2-amino-6-chlorobenzothiazole (78 mg, 0.42 mmol) as substrates, the reaction was performed in the same manner as above, thereby obtaining 113 mg of 2-(3-(3,4-dimethoxyphenyl)propanamide)-6-chlorobenzothiazole in a yield of 72%.

$^1$H NMR (CDCl$_3$): δ9.41 (s, 1H), 7.79 (d, J=2.9 Hz, 1H), 7.62 (d, J=11.7 Hz, 1H), 7.37 (dd, J=2.6, 11.4 Hz, 1H), 6.80-6.67 (m, 3H), 3.85 (s, 3H), 3.82 (s, 3H), 3.03 (t, J=9.9 Hz, 2H), 2.77 (t, J=9.9 Hz, 2H)

MS(ESI) Found: 399 [M+H]$^+$

KY02114

Using 4-(3,4-dimethoxyphenyl)butanoyl chloride (100 mg, 0.41 mmol) and 2-amino-6-chlorobenzothiazole (76 mg, 0.41 mmol) as substrates, the reaction was performed in the same manner as above, thereby obtaining 121 mg of 2-(4-(3,4-dimethoxyphenyl)butanamide)-6-chlorobenzothiazole in a yield of 75%.

$^1$H NMR (CDCl$_3$): δ9.15 (s, 1H), 7.79 (d, J=2.9 Hz, 1H), 7.64 (d, J=11.3 Hz, 1H), 7.39 (dd, J=2.6, 11.4 Hz, 1H), 6.80-6.68 (m, 3H), 3.87 (s, 3H), 3.84 (s, 3H), 2.67 (t, J=9.9 Hz, 2H), 2.48 (t, J=9.9 Hz, 2H), 2.09 (m, 2H)

MS (ESI) Found: 413 [M+H]$^+$

KY01045

Using 5-(3,4-dimethoxyphenyl)pentanoyl chloride (30 mg, 0.13 mmol) and 2-amino-6-chlorobenzothiazole (23 mg, 0.13 mmol) as substrates, the reaction was performed in the same manner as above, thereby obtaining 39 mg of 2-(5-(3,4-dimethoxyphenyl)pentanamide)-6-chlorobenzothiazole in a yield of 75%.

$^1$H NMR (CDCl$_3$): δ8.91 (s, 1H), 7.79 (d, J=8.7 Hz, 1H), 7.66 (d, J=8.7 Hz, 1H), 7.49 (dd, J=2.3, 8.7 Hz, 1H), 6.79 (d, J=7.8 Hz, 1H), 6.71 (d, J=7.8 Hz, 1H) 6.70 (s, 1H), 3.87 (s, 3H), 3.86 (s, 3H), 2.62 (t, J=7.4 Hz, 2H), 2.52 (t, J=7.3 Hz, 2H), 1.80 (m, 2H), 1.72 (m, 2H)

MS (ESI) Found: 405 [M+H]$^+$

KY01040

Using 3,4-dimethoxybenzoylyl chloride (100 mg, 0.5 mmol) and 2-amino-6-nitrobenzothiazole (105 mg, 0.57 mmol) as substrates, the reaction was performed in the same manner as above, thereby obtaining 100 mg of 2-(3,4-dimethoxybenzamide)-6-nitrobenzothiazole in a yield of 56%.

$^1$H NMR (CDCl$_3$): δ10.15 (s, 1H), 8.80 (d, J=2.3 Hz, 1H), 8.31 (dd, J=2.3, 9.2 Hz, 1H), 7.73 (d, J=9.2 Hz, 1H), 7.63-7.47 (m, 2H), 6.95 (d, J=8.7 Hz, 1H), 3.98 (s, 3H), 3.97 (s, 3H)

MS (ESI) Found: 360 [M+H]$^+$

KY02109

Using 2-(3,4-dimethoxyphenyl)acetyl chloride (100 mg, 0.51 mmol) and 2-amino-6-chlorobenzothiazole (94 mg, 0.51 mmol) as substrates, the reaction was performed in the same manner as above, thereby obtaining 153 mg of 2-(2-(3,4-dimethoxyphenyl)acetamide)-6-chlorobenzothiazole in a yield of 83%.

$^1$H NMR (CDCl$_3$): δ8.91 (s, 1H), 8.75 (s, 1H), 8.31 (dd, J=12.1 Hz, 1H), 7.77 (d, J=11.7 Hz, 1H), 7.00-6.70 (m, 3H), 3.92 (s, 3H), 3.90 (s, 3H), 3.86 (s, 2H)

MS (ESI) Found: 396 [M+H]$^+$

KY01042

Using 3-(3,4-dimethoxyphenyl)propanoyl chloride (100 mg, 0.5 mmol) and 2-amino-6-nitrobenzothiazole (105 mg, 0.57 mmol) as substrates, the reaction was performed in the same manner as above, thereby obtaining 138 mg of 2-(3-(3,4-dimethoxyphenyl)propanamide)-6-nitrobenzothiazole in a yield of 71%.

$^1$H NMR (CDCl$_3$): δ9.29 (s, 1H), 8.75 (d, J=1.8 Hz, 1H), 8.31 (dd, J=2.3, 9.2 Hz, 1H), 7.77 (d, J=9.2 Hz, 1H), 6.80 (d,

J=8.7 Hz, 1H), 6.75 (d, J=8.7 Hz, 1H), 6.74 (s, 1H), 3.85 (s, 3H), 3.84 (s, 3H), 3.06 (t, J=7.3 Hz, 2H), 2.83 (t, J=7.8 Hz, 2H)

MS (ESI) Found: 388 [M+H]$^+$

KY01043

Using 4-(3,4-dimethoxyphenyl)butanoyl chloride (55 mg, 0.25 mmol) and 2-amino-6-nitrobenzothiazole (50 mg, 0.25 mmol) as substrates, the reaction was performed in the same manner as above, thereby obtaining 65 mg of 2-(4-(3,4-dimethoxyphenyl)butanamide)-6-nitrobenzothiazole in a yield of 66%.

$^1$H NMR (CDCl$_3$): δ8.75 (d, J=2.3 Hz, 1H), 8.29 (dd, J=2.3, 8.7 Hz, 1H), 7.70 (d, J=8.7 Hz, 1H), 6.75 (d, J=8.7 Hz, 1H), 6.67 (s, 1H), 6.66 (d, J=8.7 Hz, 1H), 3.83 (s, 3H), 3.83 (s, 3H), 2.66 (t, J=7.4 Hz, 2H), 2.54 (t, J=7.3 Hz, 2H), 2.11 (m, 2H)

MS (ESI) Found: 402 [M+H]$^+$

KY01046

Using 5-(3,4-dimethoxyphenyl)pentanoyl chloride (30 mg, 0.13 mmol) and 2-amino-6-nitrobenzothiazole (25 mg, 0.13 mmol) as substrates, the reaction was performed in the same manner as above, thereby obtaining 38 mg of 2-(5-(3,4-dimethoxyphenyl)pentanamide)-6-nitrobenzothiazole in a yield of 70%.

$^1$H NMR (CDCl$_3$): δ8.94 (s, 1H), 8.75 (d, J=2.3 Hz, 1H), 8.32 (dd, J=2.3, 9.2 Hz, 1H), 7.81 (d, J=9.2 Hz, 1H), 6.80 (d, J=7.8 Hz, 1H), 6.72 (d, J=7.8 Hz, 1H) 6.71 (s, 1H), 3.88 (s, 3H), 3.86 (s, 3H), 2.63 (t, J=7.4 Hz, 2H), 2.56 (t, J=7.3 Hz, 2H), 1.82 (m, 2H), 1.73 (m, 2H)

MS (ESI) Found: 416 [M+H]$^+$

KY02104

Using 2-(3,4-dimethoxyphenyl)acetyl chloride (100 mg, 0.51 mmol) and 2-amino-6-fluorobenzothiazole (86 mg, 0.51 mmol) as substrates, the reaction was performed in the same manner as above, thereby obtaining 157 mg of 2-(2-(3,4-dimethoxyphenyl)acetamide)-6-fluorobenzothiazole in a yield of 89%.

$^1$H NMR (CDCl$_3$): δ9.14 (s, 1H), 7.04 (dd, J=6.2, 12.1 Hz, 1H), 7.50 (dd, J=3.6, 11.0 Hz, 1H), 7.14 (ddt, J=3.7, 12.1 Hz, 1H), 6.90-6.78 (m, 3H), 3.90 (s, 3H), 3.87 (s, 3H), 3.80 (s, 2H)

MS (ESI) Found: 369 [M+H]$^+$

SO087

An N,N'-dimethylformamide (5 ml) solution containing 2-amino-6-bromobenzothiazole (500 mg, 2.18 mmol), 3-(3,4-dimethoxyphenyl)propionic acid (505 mg, 2.40 mmol), O-(6-chlorobenzotriazol-1-yl)-N,N,N',N'-tetramethyluronium hexafluorophosphate (1.09 g, 2.63 mmol) and N,N'-diisopropylethylamine (419 μl, 2.41 mmol) was stirred overnight at room temperature. After completion of the reaction, the reaction solution was diluted with ethyl acetate and washed with a saturated sodium hydrogen carbonate aqueous solution, distilled water and a saturated sodium chloride aqueous solution. The solution was dried over sodium sulfate and the solvent was then evaporated. The residue was refluxed in ethanol and recrystallized, thereby obtaining 320 mg of 2-(3-(3,4-dimethoxyphenyl)propanamide)-6-bromobenzothiazole in a yield of 35%.

$^1$H NMR (DMSO-d$_6$): δ12.45 (s, 1H), 8.25 (d, J=1.8 Hz, 1H), 7.66 (d, J=8.4 Hz, 1H), 7.56 (dd, J=1.8, 8.4 Hz, 1H), 6.87-6.83 (m, 2H), 6.77-6.73 (m, 1H), 3.71 (s, 3H), 3.70 (s, 3H), 2.88 (t, J=7.0 Hz, 2H), 2.79 (t, J=7.0 Hz, 2H)

SO102

Using 2-amino-6-chlorobenzothiazole (55 mg, 0.298 mmol) and 3-(3,4-dimethoxyphenyl)propionic acid (80 mg, 0.357 mmol) as substrates, the reaction was performed in the same manner as SO087, thereby obtaining 40 mg of N-(6-chlorobenzothiazol-2-yl)-3-(4-ethoxy-3-methoxyphenyl)propanamide in a yield of 34%.

$^1$H NMR (DMSO-d$_6$): δ12.44 (s, 1H), 8.11 (d, J=2.2 Hz, 1H), 7.71 (d, J=8.8 Hz, 1H), 7.44 (dd, J=2.2, 8.8 Hz, 1H), 6.90-6.82 (m, 2H), 6.72 (dd, J=1.8, 7.0 Hz), 3.94 (q, J=7.0 Hz, 2H), 3.72 (s, 3H), 2.91-2.85 (m, 2H), 2.82-2.75 (m, 2H), 1.28 (t, J=7.0 Hz, 3H)

SO094

Sodium hydride (60%) (106 mg, 2.65 mmol) was added while stirring under ice cooling to an N,N'-dimethylformamide (7 ml) solution containing 2-amino-6-hydroxybenzothiazole (400 mg, 2.41 mmol) under an argon atmosphere and stirred for 30 minutes, and then 4-bromoethyl butyrate (521 μl, 3.62 mmol) was added thereto and stirred overnight at room temperature. After completion of the reaction, the reaction solution was diluted with ethyl acetate and washed with a saturated ammonium chloride aqueous solution and a saturated sodium chloride aqueous solution. The solution was dried over sodium sulfate and the solvent was evaporated, thereby obtaining 372 mg of ethyl 4-((2-aminobenzothiazol-6-yl) (oxy)butanoate in a yield of 55%.

An N,N'-dimethylformamide (5 ml) solution containing ethyl 4-((2-aminobenzothiazol-6-yl)oxy)butanoate (372 mg, 1.33 mmol), 3-(3,4-dimethoxyphenyl)propionic acid (335 mg, 1.59 mmol), O-(6-chlorobenzotriazol-1-yl)-N,N,N',N'-tetramethyluronium hexafluorophosphate (639 mg, 1.59 mmol) and N,N'-diisopropylethylamine (278 μl, 1.59 mmol) was stirred overnight at room temperature. After completion of the reaction, the reaction solution was diluted with ethyl acetate and washed with a saturated sodium hydrogen carbonate aqueous solution, distilled water and a saturated sodium chloride aqueous solution. The solution was dried over sodium sulfate and the solvent was evaporated. The residue was refluxed in ethanol and recrystallized, thereby obtaining 447 mg of ethyl 4-((2-(3-(3,4-dimethoxyphenyl)propanamide)benzothiazol-6-yl)oxy)butanoate in a yield of 76%.

5 N NaOH Aqueous solution (378 μl) was added to a 1,4-dioxane solution containing ethyl 4-((2-(3-(3,4-dimethoxyphenyl)propanamide)benzothiazol-6-yl)oxy)butanoate (447 mg, 0.946 mmol) and stirred overnight at room temperature. After completion of the reaction, the reaction solution was condensed and neutralized with 6 N hydrochloric acid under ice cooling. The deposit was collected by vacuum filtration and washed with water, thereby obtaining 271 mg of 4-((2-(3-(3,4dimethoxyphenyl)propanamide)benzothiazol-6-yl)oxy)butanoic acid in a yield of 64%.

1-Hydroxybenzotriazole (38 mg, 0.248 mmol) and 1-ethyl-3-(3-dimethylaminopropyl)carbodiimide hydrochloride (52 mg, 0.270 mmol) were added to an N,N'-dimethylformamide (1 ml) solution containing 4-((2-(3-(3,4-dimethoxyphenyl)propanamide)benzothiazol-6-yl)oxy) butanoic acid (100 mg, 0.225 mmol) and morpholine (22 μl, 0.248 mmol) and stirred for 2 days at room temperature. After completion of the reaction, the reaction solution was diluted with ethyl acetate and washed with a saturated sodium hydrogen carbonate aqueous solution, distilled water and a saturated sodium chloride aqueous solution. The solution was dried over sodium sulfate and the solvent was evaporated. The residue was refluxed in ethanol and recrystallized, thereby obtaining 50 mg of 3-(3,4-dimethoxyphenyl)-N-(6-(4-morpholino-4-oxobutoxy)benzothiazol-2-yl) propanamide in a yield of 43%.

$^1$H NMR (DMSO-d$_6$): δ12.20 (s, 1H), 7.60 (d, J=8.8 Hz, 1H), 7.55 (d, J=2.6 Hz, 1H), 7.01 (dd, J=2.6, 8.8 Hz, 1H), 6.86-6.83 (m, 2H), 6,75 (dd, J=1.8, 8.1 Hz), 4.03 (t, J=6.2 Hz, 2H), 3.71 (s, 3H), 3.70 (s, 3H), 3.56-3.53 (m, 4H), 3.46-3.42 (m, 4H), 2.87 (t, J=7.0 Hz), 2H), 2.75 (t, J=7.0 Hz, 2H), 2.51-2.46 (m, 2H), 1.96 (t, J=7.0 Hz, 2H)

SO096

Using 4-((2-(3-(3,4-dimethoxyphenyl)propanamide)benzothiazol-6-yl)oxy)butanoic acid (80 mg, 0.180 mmol) and 1-methylpiperazine (21.8 μl, 0.198 mmol) as substrates, the reaction was performed in the same manner as SO094, thereby obtaining 30 mg of 3-(3,4-dimethoxyphenyl)-N-(6-(4-(4-methylpiperazin-1-yl)-4oxobutoxy)benzothiazol-2-yl)propanamide in a yield of 41%.

$^1$H NMR (DMSO-$d_6$): δ12.20 (br s, 1H), 7.54 (d, J=8.8 Hz, 1H), 7.48 (d, J=2.6 Hz, 1H), 6.96 (dd, J=2.6, 8.8 Hz, 1H), 6.86-6.82 (m, 2H), 6.73 (dd, J=1.8, 8.1 Hz, 1H), 4.01 (t, J=6.2 Hz, 2H), 3.71 (s, 3H), 3.69 (s, 3H), 3.45-3.41 (m, 4H), 2.86 (t, J=7.7 Hz, 2H), 2.70 (t, J=7.7 Hz, 2H), 2.50-2.45 (m, 2H), 2.29-2.20 (m, 4H), 2.15 (s, 3H), 1.94 (t, J=7.0 Hz, 2H)

CITED REFERENCES

Non-patent Literature

1. Suemori, H. et al. Efficient establishment of human embryonic stem cell lines and long-term maintenance with stable karyotype by enzymatic bulk passage. Biochem Biophys Res Commun 345, 926-932 (2006).
2. Smith, K. P., Luong, M. X. & Stein, G. S. Pluripotency: toward a gold standard for human ES and iPS cells. J Cell Physiol 220, 21-29 (2009).
3. Yamashita, J. K., ES and iPS cell research for cardiovascular regeneration. Exp Cell Res 316, 2555-2559 (2010).
4. Yoshida, Y. & Yamanaka, S. iPS cells: a source of cardiac regeneration. J Mol Cell Cardiol 50, 327-332 (2011).
5. Lutolf, M. P., Gilbert, P. M. & Blau, H. M. Designing materials to direct stem-cell fate. Nature 462, 433-441 (2009).
6. Irion, S., Nostro, M. C., Kattman, S. J. & Keller, G. M. Directed differentiation of pluripotent stem cells: from developmental biology to therapeutic applications. Cold Spring Harb Symp Quant Biol 73, 101-110 (2008).
7. Chien, K. R., Moretti, A. & Laugwitz, K. L. Development. ES cells to the rescue. Science 306, 239-240 (2004).
8. Menasche, P. Stem cell therapy for heart failure: are arrhythmias a real safety concern? Circulation 119, 2735-2740 (2009).
9. Passier, R., van Laake, L. W. & Mummery, C. L. Stem-cell-based therapy and lessons from the heart. Nature 453, 322-329 (2008).
10. Segers, V. F. & Lee, R. T. Stem-cell therapy for cardiac disease. Nature 451, 937-942 (2008).
11. Srivastava, D. & Ivey, K. N. Potential of stem-cell-based therapies for heart disease. Nature 441, 1097-1099 (2006).
12. Chien, K. R., Domian, I. J. & Parker, K. K. Cardiogenesis and the complex biology of regenerative cardiovascular medicine. Science 322, 1494-1497 (2008).
13. Laflamme, M. A. & Murry, C. E. Heart regeneration. Nature 473, 326-335 (2011).
14. Hansson, E. M., Lindsay, M. E. & Chien, K. R. Regeneration next: toward heart stem cell therapeutics. Cell Stem Cell 5, 364-377 (2009).
15. Rajala, K., Pekkanen-Mattila, M. & Aalto-Setala, K. Cardiac differentiation of pluripotent stem cells. Stem Cells Int 2011, 383709 (2011).
16. Yang, L. et al. Human cardiovascular progenitor cells develop from a KDR+ embryonic-stem-cell-derived population. Nature 453, 524-528 (2008).
17. Paige, S. L. et al. Endogenous Wnt/beta-catenin signaling is required for cardiac differentiation in human embryonic stem cells. PLoS One 5, e11134 (2010).
18. Even, M. S., Sandusky, C. B. & Barnard, N. D. Serum-free hybridoma culture: ethical, scientific and safety considerations. Trends Biotechnol 24, 105-108 (2006).
19. Kattman, S. J. et al. Stage-specific optimization of activin/nodal and BMP signaling promotes cardiac differentiation of mouse and human pluripotent stem cell lines. Cell Stem Cell 8, 228-240 (2011).
20. Burridge, P. W. et al. A universal system for highly efficient cardiac differentiation of human induced pluripotent stem cells that eliminates interline variability. PLoS One 6, e18293 (2011).
21. Xu, Y., Shi, Y. & Ding, S. A chemical approach to stem-cell biology and regenerative medicine. Nature 453, 338-344 (2008).
22. Chen, B. et al. Small molecule-mediated disruption of Wnt-dependent signaling in tissue regeneration and cancer. Nat Chem. Biol 5, 100-107 (2009).
23. Ichida, J. K. et al. A small-molecule inhibitor of tgf-Beta signaling replaces sox2 in reprogramming by inducing nanog. Cell Stem Cell 5, 491-503 (2009).
24. Sato, A., Kawazoe, Y., Kamisuki, S. & Uesugi, M. Synthesis of synthetic small molecule transcription factors (STF). Nucleic Acids Symp Ser (Oxf), 29-30 (2006).
25. Kamisuki, S. et al. A small molecule that blocks fat synthesis by inhibiting the activation of SREBP. Chem Biol 16, 882-892 (2009).
26. Graichen, R. et al. Enhanced cardiomyogenesis of human embryonic stem cells by a small molecular inhibitor of p38 MAPK. Differentiation 76, 357-370 (2008).
27. Hao, J. et al. Dorsomorphin, a selective small molecule inhibitor of BMP signaling, promotes cardiomyogenesis in embryonic stem cells. PLoS One 3, e2904 (2008).
28. Naito, A. T. et al. Developmental stage-specific biphasic roles of Wnt/beta-catenin signaling in cardiomyogenesis and hematopoiesis. Proc Natl Acad Sci USA 103, 19812-19817 (2006).
29. Qyang, Y. et al. The renewal and differentiation of Isl1+ cardiovascular progenitors are controlled by a Wnt/beta-catenin pathway. Cell Stem Cell 1, 165-179 (2007).
30. Ren, Y. et al. Small molecule Wnt inhibitors enhance the efficiency of BMP-4-directed cardiac differentiation of human pluripotent stem cells. J Mol Cell Cardiol 51, 280-287 (2011).
31. Wang, H., Hao, J. & Hong, C. C. Cardiac induction of embryonic stem cells by a small molecule inhibitor of Wnt/beta-catenin signaling. ACS Chem Biol 6, 192-197 (2011).
32. Willems, E. et al. Small-molecule inhibitors of the Wnt pathway potently promote cardiomyocytes from human embryonic stem cell-derived mesoderm. Circ Res 109, 360-364 (2011).
33. Otsuji, T. G. et al. Progressive maturation in contracting cardiomyocytes derived from human embryonic stem cells: Qualitative effects on electrophysiological responses to drugs. Stem Cell Res 4, 201-213 (2010).
34. Suessbrich, H., Waldegger, S., Lang, F. & Busch, A. E. Blockade of HERG channels expressed in Xenopus oocytes by the histamine receptor antagonists terfenadine and astemizole. FEBS Lett 385, 77-80 (1996).
35. Gotea, V. & Ovcharenko, I. DiRE: identifying distant regulatory elements of co-expressed genes. Nucleic Acids Res 36, W133-139 (2008).

36. Zhu, W. et al. IGFBP-4 is an inhibitor of canonical Wnt signalling required for cardiogenesis. Nature 454, 345-349 (2008).
37. Mignone, J. L., Kreutziger, K. L., Paige, S. L. & Murry, C. E. Cardiogenesis from human embryonic stem cells. Circ J 74, 2517-2526 (2010).
38. Sato, S., Murata, A., Shirakawa, T. & Uesugi, M. Biochemical target isolation for novices: affinity-based strategies. Chem Biol 17, 616-623 (2010).
39. Jacot, J. G., Martin, J. C. & Hunt, D. L. Mechanobiology of cardiomyocyte development. J Biomech 43, 93-98 (2010).
40. Asai, Y., Tada, M., Otsuji, T. G., & Nakatsuji, N. Combination of functional cardiomyocytes derived from human stem cells and a highly-efficient microelectrode array system: an ideal hybrid model assay for drug development. Curr Stem Cell Res Ther 5, 227-232 (2010).
41. Thomson, J. A. et al. Embryonic stem cell lines derived from human blastocysts. Science 282, 1145-1147 (1998).
42. Takahashi, K. et al. Induction of pluripotent stem cells from adult human fibroblasts by defined factors. Cell 131, 861-872 (2007).
43. Yu, J. et al. Induced pluripotent stem cell lines derived from human somatic cells. Science 318, 1917-1920 (2007).
44. Suemori, H. & Nakatsuji, N. Generation and characterization of monkey embryonic stem cells. Methods Mol Biol 329, 81-89 (2006).
45. Suemori, H. et al. Establishment of embryonic stem cell lines from cynomolgus monkey blastocysts produced by IVF or ICSI. Dev Dyn 222, 273-279 (2001).
46. Yuasa, S. et al. Transient inhibition of BMP signaling by Noggin induces cardiomyocyte differentiation of mouse embryonic stem cells. Nat Biotechnol 23, 607-611 (2005).
47. Murakami, G. et al. Chemical library screening identifies a small molecule that downregulates SOD1 transcription for drugs to treat amyotrophic lateral sclerosis. J Biomol Screen 16, 405-414 (2011).

The above references are herein incorporated by reference.

SEQUENCE LISTING FREE TEXT

SEQ ID NO: 1: Primer
SEQ ID NO: 2: Primer
SEQ ID NO: 3: Primer
SEQ ID NO: 4: Primer
SEQ ID NO: 5: Primer
SEQ ID NO: 6: Primer
SEQ ID NO: 7: Primer
SEQ ID NO: 8: Primer
SEQ ID NO: 9: Primer
SEQ ID NO: 10: Primer
SEQ ID NO: 21: primer
SEQ ID NO: 22: Primer
SEQ ID NO: 23: Primer
SEQ ID NO: 24: Primer
SEQ ID NO: 25: Primer
SEQ ID NO: 26: Primer
SEQ ID NO: 27: Primer
SEQ ID NO: 28: Primer
SEQ ID NO: 29: Primer
SEQ ID NO: 30: Primer
SEQ ID DO; 31: Primer
SEQ ID KO: 32: Primer
SEQ ID NO: 33: Primer
SEQ ID NO: 34: Primer
SEQ ID NO: 35: Primer
SEQ ID NO: 36: Primer

What is claimed is:

1. A method for inducing cardiac differentiation of a pluripotent stem cell, which comprises the steps of
   (1) culturing the pluripotent stem cell in a medium containing one or more WNT signaling activators, and
   (2) replacing the medium from step (1) with a medium containing one or more WNT signaling inhibitors wherein a plurality of cardiac differentiated cells are produced,
   wherein said one or more WNT signaling inhibitors comprise the compound of Formula (I):

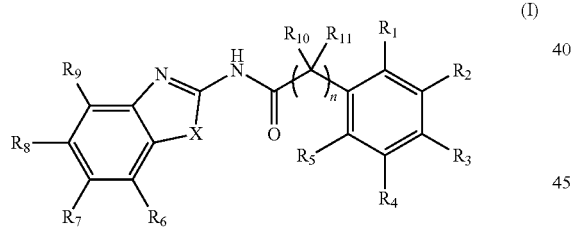

(I)

wherein
   $R_1$ to $R_5$ are each independently a hydrogen atom; a halogen atom; a hydroxyl group; a linear or branched alkoxy group having 1 to 5 carbon atoms; a linear or branched alkyl group having 1 to 5 carbon atoms which is unsubstituted or substituted with a halogen atom; or a group —$NR_{12}R_{13}$, wherein $R_{12}$ and $R_{13}$ are each independently a hydrogen atom, an oxygen atom, or a linear or branched alkyl group having 1 to 5 carbon atoms which is unsubstituted or substituted with a halogen atom; wherein two adjacent groups among $R_1$ to $R_5$ may join together to form —O—$CH_2$—O— or —O—$(CH_2)_2$—O—,
   $R_6$ to $R_9$ are each independently a hydrogen atom; a halogen atom; a hydroxyl group; a linear or branched alkoxy group having 1 to 5 carbon atoms; a linear or branched alkoxy group having 1 to 5 carbon atoms which is substituted with a group —C(O)A, wherein A is a saturated or unsaturated 5- or 6-membered ring which is unsubstituted or substituted with a linear or branched alkyl group having 1 to 5 carbon atoms and the ring may contain 1 or 2 atoms independently selected from a nitrogen atom, an oxygen atom and a sulfur atom; a linear or branched alkyl group having 1 to 5 carbon atoms which is unsubstituted or substituted with a halogen atom; or a group —$NR_{12}R_{13}$, wherein $R_{12}$ and $R_{13}$ are each independently a hydrogen atom, an oxygen atom, or a linear or branched alkyl group having 1 to 5 carbon atoms which is unsubstituted or substituted with a halogen atom; wherein two adjacent groups among $R_6$ to $R_9$ may join together to form —O—$CH_2$—O— or —O—$(CH_2)_2$—O—,
   $R_{10}$ to $R_{11}$ are each independently a hydrogen atom; or a linear or branched alkyl group having 1 to 5 carbon atoms,
   X is a sulfur atom, and
   n is an integer of 0 to 6,
or a salt thereof.

2. The method of claim 1, wherein said compound of Formula (I) is selected from the group consisting of

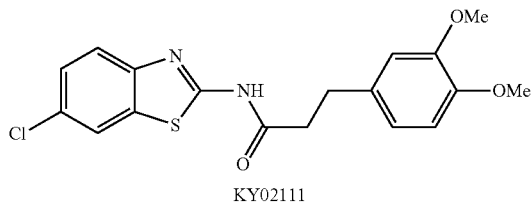

KY02111

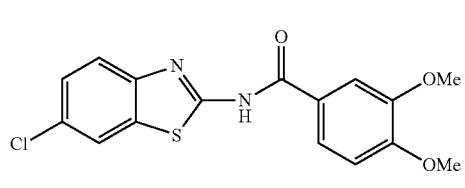

KY01041

-continued
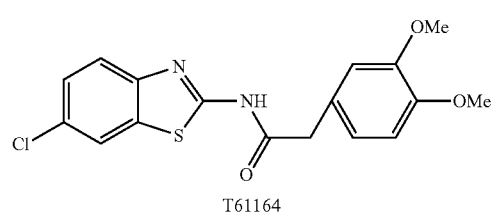
T61164
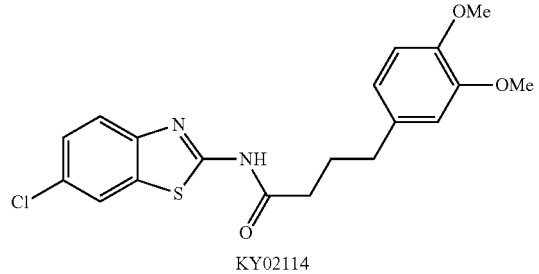
KY02114
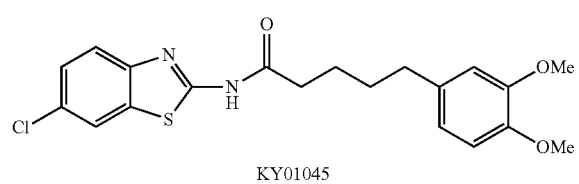
KY01045
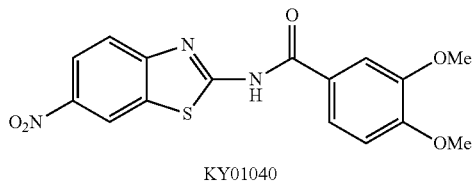
KY01040
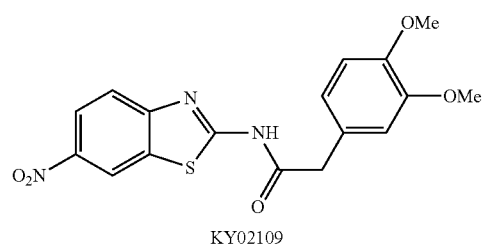
KY02109
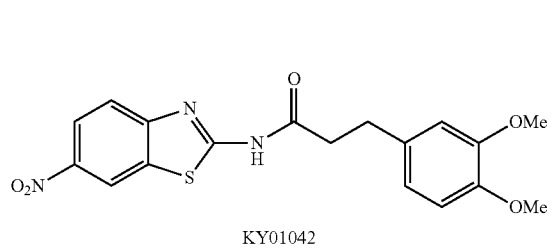
KY01042
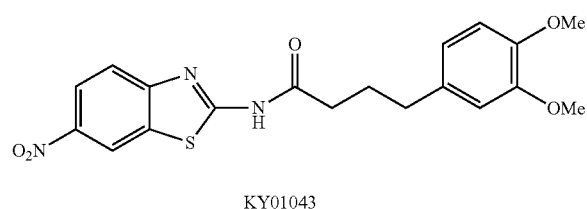
KY01043
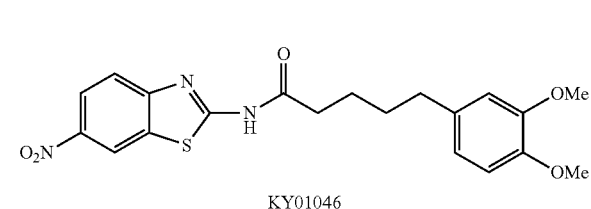
KY01046
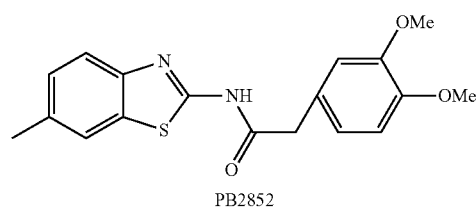
PB2852
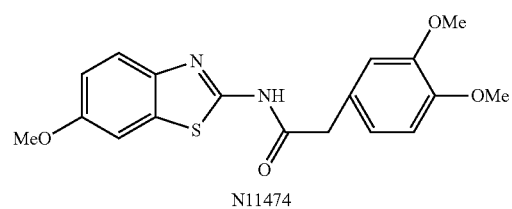
N11474
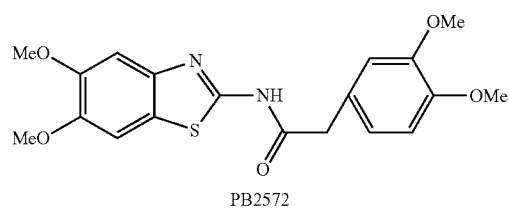
PB2572
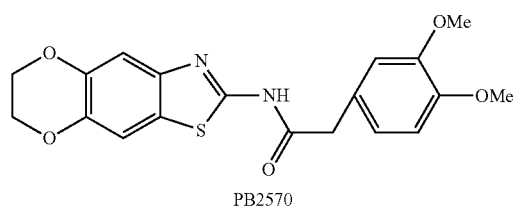
PB2570
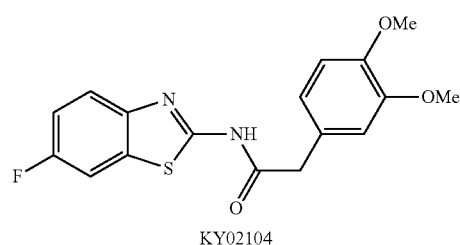
KY02104
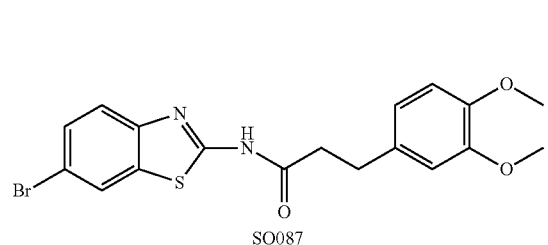
SO087

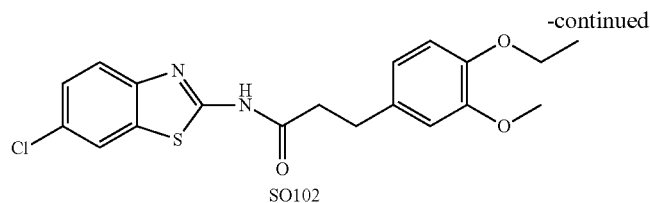

or a salt thereof.

3. The method of claim 2, wherein the one or more WNT signaling inhibitors comprise

KY02111 or a salt thereof.

4. The method of claim 1, wherein the one or more WNT signaling inhibitors further comprise a WNT signaling inhibitor selected from XAV939 and IWP-2.

5. The method of claim 1, wherein the one or more WNT signaling activators comprise a GSK3β inhibitor.

6. The method of claim 5, wherein the GSK3β inhibitor is selected from BIO and CHIR99021.

7. The method of claim 1, wherein the medium in the step (1) and the medium in the step (2) do not comprise serum.

8. The method of claim 1, wherein the medium in the step (1) and the medium in the step (2) do not comprise a cytokine.

9. The method of claim 1, wherein the medium in the step (1) and the medium in the step (2) comprise albumin.

10. The method of claim 1, wherein the medium in the step (1) and the medium in the step (2) do not comprise a protein other than albumin.

11. The method of claim 1, wherein the two culturing steps are conducted in the absence of a xenogeneic component.

12. The method of claim 1, wherein the pluripotent stem cell is a monkey or human pluripotent stem cell.

13. The method of claim 1, wherein the differentiated cells include a cardiomyocyte.

14. A kit for promoting cardiac differentiation comprising one or more WNT signaling activators and/or one or more WNT signaling inhibitors, wherein the kit is used for the method of claim 1, wherein said one or more WNT signaling inhibitors comprise the compound of Formula (I):

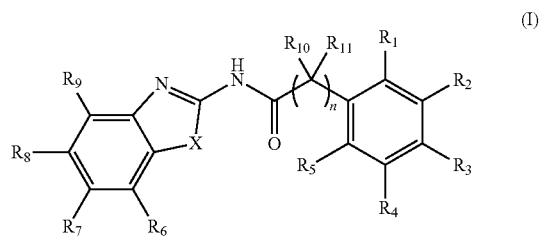

wherein $R_1$ to $R_5$ are each independently a hydrogen atom; a halogen atom; a hydroxyl group; a linear or branched alkoxy group having 1 to 5 carbon atoms; a linear or branched alkyl group having 1 to 5 carbon atoms which is unsubstituted or substituted with a halogen atom; or a group —$NR_{12}R_{13}$, wherein $R_{12}$, and $R_{13}$ are each independently a hydrogen atom, an oxygen atom, or a linear or branched alkyl group having 1 to 5 carbon atoms which is unsubstituted or substituted with a halogen atom; wherein two adjacent groups among $R_1$ to $R_5$ may join together to form —O—$CH_2$—O— or —O—$(CH_2)_2$—O—, $R_6$ to $R_9$ are each independently a hydrogen atom; a halogen atom; a hydroxyl group; a linear or branched alkoxy group having 1 to 5 carbon atoms; a linear or branched alkoxy group having 1 to 5 carbon atoms which is substituted with a group —C(O)A, wherein A is a saturated or unsaturated 5- or 6-membered ring which is unsubstituted or substituted with a linear or branched alkyl group having 1 to 5 carbon atoms and the ring may contain 1 or 2 atoms independently selected from a nitrogen atom, an oxygen atom and a sulfur atom; a linear or branched alkyl group having 1 to 5 carbon atoms which is unsubstituted or substituted with a halogen atom; or a group —$NR_{12}R_{13}$, wherein $R_{12}$, and $R_{13}$ are each independently a hydrogen atom, an oxygen atom, or a linear or branched alkyl group having 1 to 5 carbon atoms which is unsubstituted or substituted with a halogen atom; wherein two adjacent groups among $R_6$ to $R_9$ may join together to form —O—$CH_2$—O— or —O—$(CH_2)_2$—O—, $R_{10}$ to $R_{11}$ are each independently a hydrogen atom; or a linear or branched alkyl group having 1 to 5 carbon atoms, X is a sulfur atom, and n is an integer of 0 to 6, or a salt thereof.

15. The method of claim 1, wherein $R_1$, $R_4$, $R_5$, $R_6$ and $R_9$ each are a hydrogen atom, $R_2$ and $R_3$ are a methoxy group, an ethoxy group or a propoxy group, $R_{10}$ and $R_{11}$ are a hydrogen atom, and n is an integer of 0 to 4.

16. The method of claim 15, wherein $R_7$ is a halogen atom, and $R_8$ is a hydrogen atom.

17. The method of claim 16, wherein n is 2 or 3.

18. The method of claim 17, wherein $R_2$ and $R_3$ are a methoxy group.

* * * * *

SEQUENCE LISTING

```
<160> NUMBER OF SEQ ID NOS: 38

<210> SEQ ID NO 1
<211> LENGTH: 22
<212> TYPE: DNA
<213> ORGANISM: Artificial Sequence
<220> FEATURE:
<223> OTHER INFORMATION: Primer

<400> SEQUENCE: 1
acccctcgga ccataggatt ac                                              22

<210> SEQ ID NO 2
<211> LENGTH: 21
<212> TYPE: DNA
<213> ORGANISM: Artificial Sequence
<220> FEATURE:
<223> OTHER INFORMATION: Primer

<400> SEQUENCE: 2
aaggcgcact gaagttctgt g                                               21

<210> SEQ ID NO 3
<211> LENGTH: 22
<212> TYPE: DNA
<213> ORGANISM: Artificial Sequence
<220> FEATURE:
<223> OTHER INFORMATION: Primer

<400> SEQUENCE: 3
```
caacctcact gacggtgaaa aa                                           22

<210> SEQ ID NO 4
<211> LENGTH: 23
<212> TYPE: DNA
<213> ORGANISM: Artificial Sequence
<220> FEATURE:
<223> OTHER INFORMATION: Primer

<400> SEQUENCE: 4
acaaattctg gtgtgccaaa gtt                                          23

<210> SEQ ID NO 5
<211> LENGTH: 20
<212> TYPE: DNA
<213> ORGANISM: Artificial Sequence
<220> FEATURE:
<223> OTHER INFORMATION: Primer

<400> SEQUENCE: 5
ccttggatgg gtattccaga                                              20

<210> SEQ ID NO 6
<211> LENGTH: 20
<212> TYPE: DNA
<213> ORGANISM: Artificial Sequence
<220> FEATURE:
<223> OTHER INFORMATION: Primer

<400> SEQUENCE: 6
cctgaggcac agtctgatga                                              20

<210> SEQ ID NO 7
<211> LENGTH: 20
<212> TYPE: DNA
<213> ORGANISM: Artificial Sequence
<220> FEATURE:
<223> OTHER INFORMATION: Primer

<400> SEQUENCE: 7
tgttggggag gagtttcatc                                              20

<210> SEQ ID NO 8
<211> LENGTH: 20
<212> TYPE: DNA
<213> ORGANISM: Artificial Sequence
<220> FEATURE:
<223> OTHER INFORMATION: Primer

<400> SEQUENCE: 8
gcacaacaag tggaagggac                                              20

<210> SEQ ID NO 9
<211> LENGTH: 22
<212> TYPE: DNA
<213> ORGANISM: Artificial Sequence
<220> FEATURE:
<223> OTHER INFORMATION: Primer

<400> SEQUENCE: 9
ccaacaacta caacgcctac ga                                           22

<210> SEQ ID NO 10
<211> LENGTH: 22
<212> TYPE: DNA
<213> ORGANISM: Artificial Sequence

```
<220> FEATURE:
<223> OTHER INFORMATION: Primer

<400> SEQUENCE: 10
cccttcttgg tcttcccatt ct                                              22

<210> SEQ ID NO 11
<211> LENGTH: 23
<212> TYPE: DNA
<213> ORGANISM: Artificial Sequence
<220> FEATURE:
<223> OTHER INFORMATION: Primer

<400> SEQUENCE: 11
cccaagcccc atagtgccca aag                                             23

<210> SEQ ID NO 12
<211> LENGTH: 21
<212> TYPE: DNA
<213> ORGANISM: Artificial Sequence
<220> FEATURE:
<223> OTHER INFORMATION: Primer

<400> SEQUENCE: 12
caggggaggc atcgcagggt c                                               21

<210> SEQ ID NO 13
<211> LENGTH: 19
<212> TYPE: DNA
<213> ORGANISM: Artificial Sequence
<220> FEATURE:
<223> OTHER INFORMATION: Primer

<400> SEQUENCE: 13
ggtaccccga catccactt                                                  19

<210> SEQ ID NO 14
<211> LENGTH: 20
<212> TYPE: DNA
<213> ORGANISM: Artificial Sequence
<220> FEATURE:
<223> OTHER INFORMATION: Primer

<400> SEQUENCE: 14
tggaaggatt tcccactctg                                                 20

<210> SEQ ID NO 15
<211> LENGTH: 20
<212> TYPE: DNA
<213> ORGANISM: Artificial Sequence
<220> FEATURE:
<223> OTHER INFORMATION: Primer

<400> SEQUENCE: 15
ctcaagctca tggccactct                                                 20

<210> SEQ ID NO 16
<211> LENGTH: 21
<212> TYPE: DNA
<213> ORGANISM: Artificial Sequence
<220> FEATURE:
<223> OTHER INFORMATION: Primer

<400> SEQUENCE: 16
gcctcctttg cttttaccac t                                               21
```

```
<210> SEQ ID NO 17
<211> LENGTH: 20
<212> TYPE: DNA
<213> ORGANISM: Artificial Sequence
<220> FEATURE:
<223> OTHER INFORMATION: Primer

<400> SEQUENCE: 17
acaagctgca gctaaaggtc                                              20

<210> SEQ ID NO 18
<211> LENGTH: 20
<212> TYPE: DNA
<213> ORGANISM: Artificial Sequence
<220> FEATURE:
<223> OTHER INFORMATION: Primer

<400> SEQUENCE: 18
tcaagatgtg gcaaagctac                                              20

<210> SEQ ID NO 19
<211> LENGTH: 20
<212> TYPE: DNA
<213> ORGANISM: Artificial Sequence
<220> FEATURE:
<223> OTHER INFORMATION: Primer

<400> SEQUENCE: 19
accctgagtc ccctggattt                                              20

<210> SEQ ID NO 20
<211> LENGTH: 20
<212> TYPE: DNA
<213> ORGANISM: Artificial Sequence
<220> FEATURE:
<223> OTHER INFORMATION: Primer

<400> SEQUENCE: 20
tcactcattg cacgctgcat                                              20

<210> SEQ ID NO 21
<211> LENGTH: 20
<212> TYPE: DNA
<213> ORGANISM: Artificial Sequence
<220> FEATURE:
<223> OTHER INFORMATION: Primer

<400> SEQUENCE: 21
ctgctgcttt ggtgtcagag                                              20

<210> SEQ ID NO 22
<211> LENGTH: 20
<212> TYPE: DNA
<213> ORGANISM: Artificial Sequence
<220> FEATURE:
<223> OTHER INFORMATION: Primer

<400> SEQUENCE: 22
ttcctatggg gtcatccttg                                              20

<210> SEQ ID NO 23
<211> LENGTH: 20
<212> TYPE: DNA
<213> ORGANISM: Artificial Sequence
<220> FEATURE:
<223> OTHER INFORMATION: Primer
```

-continued

<400> SEQUENCE: 23
ggtgtccatc aacaacatgg                                                      20

<210> SEQ ID NO 24
<211> LENGTH: 18
<212> TYPE: DNA
<213> ORGANISM: Artificial Sequence
<220> FEATURE:
<223> OTHER INFORMATION: Primer

<400> SEQUENCE: 24
gccttgaaga gcgcgtag                                                        18

<210> SEQ ID NO 25
<211> LENGTH: 19
<212> TYPE: DNA
<213> ORGANISM: Artificial Sequence
<220> FEATURE:
<223> OTHER INFORMATION: Primer

<400> SEQUENCE: 25
gagcaacttg tcggtgctg                                                       19

<210> SEQ ID NO 26
<211> LENGTH: 20
<212> TYPE: DNA
<213> ORGANISM: Artificial Sequence
<220> FEATURE:
<223> OTHER INFORMATION: Primer

<400> SEQUENCE: 26
gatttggcca gcttgaagac                                                      20

<210> SEQ ID NO 27
<211> LENGTH: 18
<212> TYPE: DNA
<213> ORGANISM: Artificial Sequence
<220> FEATURE:
<223> OTHER INFORMATION: Primer

<400> SEQUENCE: 27
catgctcacg gtgttcca                                                        18

<210> SEQ ID NO 28
<211> LENGTH: 18
<212> TYPE: DNA
<213> ORGANISM: Artificial Sequence
<220> FEATURE:
<223> OTHER INFORMATION: Primer

<400> SEQUENCE: 28
catgctcacg gtgttcca                                                        18

<210> SEQ ID NO 29
<211> LENGTH: 18
<212> TYPE: DNA
<213> ORGANISM: Artificial Sequence
<220> FEATURE:
<223> OTHER INFORMATION: Primer

<400> SEQUENCE: 29
ctatgctgcg ctgggagt                                                        18

<210> SEQ ID NO 30

```
<211> LENGTH: 18
<212> TYPE: DNA
<213> ORGANISM: Artificial Sequence
<220> FEATURE:
<223> OTHER INFORMATION: Primer

<400> SEQUENCE: 30
ctcgcagggg ttgtcttc                                                   18

<210> SEQ ID NO 31
<211> LENGTH: 20
<212> TYPE: DNA
<213> ORGANISM: Artificial Sequence
<220> FEATURE:
<223> OTHER INFORMATION: Primer

<400> SEQUENCE: 31
acgcttactg ccagggtgac                                                 20

<210> SEQ ID NO 32
<211> LENGTH: 18
<212> TYPE: DNA
<213> ORGANISM: Artificial Sequence
<220> FEATURE:
<223> OTHER INFORMATION: Primer

<400> SEQUENCE: 32
gccgactggc aaccagag                                                   18

<210> SEQ ID NO 33
<211> LENGTH: 19
<212> TYPE: DNA
<213> ORGANISM: Artificial Sequence
<220> FEATURE:
<223> OTHER INFORMATION: Primer

<400> SEQUENCE: 33
ccacctcaac ctcatggtg                                                  19

<210> SEQ ID NO 34
<211> LENGTH: 19
<212> TYPE: DNA
<213> ORGANISM: Artificial Sequence
<220> FEATURE:
<223> OTHER INFORMATION: Primer

<400> SEQUENCE: 34
acagtgaggg cttcccaat                                                  19

<210> SEQ ID NO 35
<211> LENGTH: 22
<212> TYPE: DNA
<213> ORGANISM: Artificial Sequence
<220> FEATURE:
<223> OTHER INFORMATION: Primer

<400> SEQUENCE: 35
atggaaatcc catcaccatc tt                                              22

<210> SEQ ID NO 36
<211> LENGTH: 18
<212> TYPE: DNA
<213> ORGANISM: Artificial Sequence
<220> FEATURE:
<223> OTHER INFORMATION: Primer

<400> SEQUENCE: 36
```

```
cgccccactt gattttgg                                         18

<210> SEQ ID NO 37
<211> LENGTH: 21
<212> TYPE: DNA
<213> ORGANISM: Artificial Sequence
<220> FEATURE:
<223> OTHER INFORMATION: Primer

<400> SEQUENCE: 37
ccaggcacct gcaccctctg g                                     21

<210> SEQ ID NO 38
<211> LENGTH: 32
<212> TYPE: DNA
<213> ORGANISM: Artificial Sequence
<220> FEATURE:
<223> OTHER INFORMATION: Primer

<400> SEQUENCE: 38
tagtcgacct tggtgcttcc cctgggtcag ag                         32
```